US012807672B2

(12) United States Patent
Tang et al.

(10) Patent No.: US 12,807,672 B2
(45) Date of Patent: Nov. 24, 2026

(54) MYELIN OLIGODENDROCYTE GLYCOPROTEIN-SPECIFIC PEPTIDE FOR THE TREATMENT OR PREVENTION OF MULTIPLE SCLEROSIS

(71) Applicant: LOMA LINDA UNIVERSITY, Loma Linda, CA (US)

(72) Inventors: Xiaolei Tang, Loma Linda, CA (US); David J. Baylink, Loma Linda, CA (US)

(73) Assignee: LOMA LINDA UNIVERSITY, Loma Linda, CA (US)

( * ) Notice: Subject to any disclaimer, the term of this patent is extended or adjusted under 35 U.S.C. 154(b) by 0 days.

(21) Appl. No.: 17/983,967

(22) Filed: Nov. 9, 2022

(65) Prior Publication Data

US 2023/0312670 A1 Oct. 5, 2023

Related U.S. Application Data

(62) Division of application No. 16/314,642, filed as application No. PCT/US2017/040484 on Jun. 30, 2017, now abandoned.

(60) Provisional application No. 62/357,891, filed on Jul. 1, 2016.

(51) Int. Cl.

| | |
|---|---|
| ***C07K 14/705*** | (2006.01) |
| ***A61K 9/00*** | (2006.01) |
| ***A61K 35/15*** | (2015.01) |
| ***A61K 38/17*** | (2006.01) |
| ***A61K 39/395*** | (2006.01) |
| ***A61K 40/19*** | (2025.01) |
| ***A61K 40/22*** | (2025.01) |
| ***A61K 40/24*** | (2025.01) |
| ***A61K 40/41*** | (2025.01) |
| ***A61P 25/00*** | (2006.01) |
| ***A61P 25/28*** | (2006.01) |
| ***C07K 14/47*** | (2006.01) |
| ***C07K 16/28*** | (2006.01) |
| ***C12N 5/0783*** | (2010.01) |
| *A61K 38/00* | (2006.01) |
| *A61K 39/00* | (2006.01) |

(52) U.S. Cl.

CPC ...... *C07K 14/70503* (2013.01); *A61K 9/0019* (2013.01); *A61K 35/15* (2013.01); *A61K 38/1709* (2013.01); *A61K 39/39541* (2013.01); *A61K 40/19* (2025.01); *A61K 40/22* (2025.01); *A61K 40/24* (2025.01); *A61K 40/416* (2025.01); *A61P 25/00* (2018.01); *A61P 25/28* (2018.01); *C07K 14/4713* (2013.01); *C07K 14/70539* (2013.01); *C07K 16/2815* (2013.01); *C12N 5/0637* (2013.01); *A61K 38/00* (2013.01); *A61K 2039/505* (2013.01); *A61K 2239/31* (2023.05); *A61K 2239/38* (2023.05); *C07K 2319/00* (2013.01)

(58) Field of Classification Search

None

See application file for complete search history.

(56) References Cited

U.S. PATENT DOCUMENTS

| | | | | |
|---|---|---|---|---|
| 2006/0239979 | A1 | 10/2006 | Serizawa et al. | |
| 2010/0267622 | A1 | 10/2010 | Jiang et al. | |
| 2012/0195921 | A1 * | 8/2012 | Loftis ................ | A61K 39/0007 |
| 2015/0010631 | A1 | 1/2015 | Getts | |
| 2015/0044245 | A1 | 2/2015 | Vandenbark et al. | |

FOREIGN PATENT DOCUMENTS

WO WO2014160465 A2 * 10/2014 ............. A61K 31/78

OTHER PUBLICATIONS

Mansilla, M.J., et al. (2015), Beneficial Effect of Tolerogenic Dendritic Cells Pulsed with MOG Autoantigen in Experimental Autoimmune Encephalomyelitis. CNS Neurosci Ther, 21: 222-230. (Year: 2015).*

Mbongue J et al. The role of dendritic cells in tissue-specific autoimmunity. J Immunol Res. 2014;2014:857143 (Year: 2014).*

Sinha S et al. CD8(+) T-Cells as Immune Regulators of Multiple Sclerosis. Front Immunol. Dec. 10, 2015;6:619. (Year: 2015).*

Beeston et al., Involvement of IFN-y and Perforin, but Not Fas/FasL Interactions in Regulatory T Cell-Mediated Suppression of Experimental Autoimmune Encephalomyelitis, J. Neuroimmunol., vol. 229, No. 1-2, Dec. 15, 2010, pp. 91-97.

Ben-Nun et al., From Classic to Spontaneous and Humanized Models of Multiple Sclerosis: Impact on Understanding Pathogenesis and Drug Development, Journal of Autoimmunity, vol. 54, Nov. 2014, pp. 33-50.

Hu et al., Analysis of Regulatory CDS T Cells in Qa-1-Deficient Mice, Nature Immunology, vol. 5, No. 5, May 2004. pp. 516-523.

(Continued)

*Primary Examiner* — Gregory S Emch

*Assistant Examiner* — Estella M. Gustilo

(74) *Attorney, Agent, or Firm* — Womble Bond Dickinson (US) LLP; Michael Samardzjia

(57) ABSTRACT

Compositions for the treatment or prevention of multiple sclerosis are provided. In some embodiments, the composition comprises an isolated peptide comprising a partial amino acid sequence of a myelin oligodendrocyte glycoprotein (MOG) protein, wherein the peptide activates regulatory T cells. In some embodiments, the composition comprises dendritic cells pulsed with a MOG peptide that activates regulatory T cells. In some embodiments, the peptide activates HLA-E-restricted regulatory $CD8^+$ T cells.

16 Claims, 10 Drawing Sheets

Specification includes a Sequence Listing.

(56) References Cited

OTHER PUBLICATIONS

Leavenworth et al., Amelioration of Arthritis Through Mobilization of Peptide-Specific CDS+ Regulatory T Cells, The Journal of Clinical Investigation, vol. 123, No. 3, Mar. 2013, pp. 1382-1389.
Lutterotti et al., Antigen-Specific Therapies in MS—Current Concepts and Novel Approaches, Journal of the Neurological Sciences, vol. 27 4, Issues 1-2, Nov. 15, 2008, pp. 18-22.
Ortega et al., Autoregulatory CDS T Cells Depend on Cognate Antigen Recognition and CD4/CD8 Myelin Determinants, Neural Neuroimmunol Neuroinflamm, vol. 2, No. 6, e170, Dec. 2015, pp. 1-9.
Panoutsakopoulou et al., Suppression of Autoimmune Disease After Vaccination with Autoreactive T Cells that Express Qa-1 Peptide Complexes, The Journal of Clinical Investigation, vol. 113, No. 8, Apr. 2004, pp. 1218-1224.
International Application No. PCT/US2017/040484, International Search Report and Written Opinion, Sep. 18, 2017, 11 pages.
Steinman, The Re-Emergence of Antigen-Specific Tolerance as a Potential Therapy for MS, Multiple Sclerosis Journal, vol. 21, No. 10, Apr. 28, 2015, pp. 1223-1238.
Tang et al., Regulation of Immunity by a Novel Population of Qa-1-restricted CD8alphaalpha+ TCRalphabeta+ T Cells, The Journal of Immunology, vol. 177, Issue 11, Dec. 1, 2006, pp. 7645-7655.
Wang et al., Targeting Non-Classical Myelin Epitopes to Treat Experimental Autoimmune Encephalomyelitis, Scientific Reports, vol. 6, No. 36064, Oct. 31, 2016, pp. 1-13.
Wu et al., The Specificity of T Cell Regulation that Enables Self-Nonself Discrimination in the Periphery, Proc. Natl. Acad. Sci. USA, vol. 106, No. 2, Jan. 13, 2009, pp. 534-549.
Yuan et al., A Novel Nanoparticle Containing MOG Peptide with BTLA Induces T Cell Tolerance and Prevents Multiple Sclerosis, Molecular Immunology, vol. 57, Issue 2, Feb. 2014, pp. 93-99.

* cited by examiner

FIG. 2A. Layout of MOG OLP IDs

| | 1 | 2 | 3 | 4 | 5 | 6 | 7 | 8 | 9 | 10 | 11 | 12 |
|---|---|---|---|---|---|---|---|---|---|---|---|---|
| A | 49 | 50 | 51 | 52 | 53 | 54 | 55 | 56 | 57 | 58 | 59 | 60 |
| B | 61 | 62 | 63 | 64 | 65 | 66 | 67 | 68 | 69 | 70 | 71 | 72 |
| C | 73 | 74 | 75 | 76 | 77 | 78 | 79 | 80 | 81 | 82 | 83 | 84 |
| D | 85 | 86 | 87 | 88 | 89 | 90 | 91 | 92 | 93 | 94 | 95 | 96 |
| E | 97 | 98 | 99 | 100 | 101 | 102 | 103 | 104 | 105 | 106 | 107 | Med |

FIG. 2C. SFCs/$10^6$ $CD8^+$ T cells: C1R.Qa-$1^b$

| | 1 | 2 | 3 | 4 | 5 | 6 | 7 | 8 | 9 | 10 | 11 | 12 |
|---|---|---|---|---|---|---|---|---|---|---|---|---|
| A | 840 | 220 | 520 | 280 | 100 | 180 | 120 | 440 | 60 | 120 | 500 | 0 |
| B | 260 | 720 | 880 | 600 | 680 | 160 | 620 | 1900 | 1000 | 860 | 840 | 380 |
| C | 200 | 460 | 780 | 360 | 600 | 540 | 1180 | 1240 | 820 | 520 | 820 | 1 |
| D | 440 | 460 | 540 | 880 | 200 | 480 | 280 | 480 | 240 | 100 | 460 | 1280 |
| E | 300 | 60 | 0 | 1 | 460 | 1 | 0 | 320 | 4760 | 1 | 220 | 0 |

FIG. 2B. SFCs/$10^6$ $CD8^+$ T cells: C1R

| | 1 | 2 | 3 | 4 | 5 | 6 | 7 | 8 | 9 | 10 | 11 | 12 |
|---|---|---|---|---|---|---|---|---|---|---|---|---|
| A | 100 | 40 | 140 | 120 | 40 | 160 | 40 | 140 | 100 | 120 | 120 | 100 |
| B | 40 | 100 | 80 | 100 | 80 | 40 | 180 | 120 | 60 | 120 | 180 | 60 |
| C | 80 | 20 | 80 | 40 | 220 | 140 | 140 | 100 | 160 | 100 | 160 | 60 |
| D | 60 | 140 | 120 | 120 | 100 | 80 | 180 | 200 | 180 | 140 | 80 | 1 |
| E | 80 | 100 | 120 | 140 | 80 | 100 | 60 | 160 | 440 | 180 | 100 | 0 |

FIG. 2D. Fold increase of SFCs/$10^6$ $CD8^+$ T cells C1R.Qa-$1^b$/C1R

| | 1 | 2 | 3 | 4 | 5 | 6 | 7 | 8 | 9 | 10 | 11 | 12 |
|---|---|---|---|---|---|---|---|---|---|---|---|---|
| A | 8 | 6 | 4 | 2 | 3 | 1 | 3 | 3 | 1 | 1 | 4 | 0 |
| B | 7 | 7 | 11 | 6 | 9 | 4 | 3 | 16 | 17 | 7 | 5 | 6 |
| C | 3 | 23 | 10 | 9 | 3 | 4 | 8 | 12 | 5 | 5 | 5 | 0 |
| D | 7 | 3 | 5 | 7 | 2 | 6 | 2 | 2 | 1 | 1 | 6 | 1280 |
| E | 4 | 1 | 0 | 0 | 6 | 0 | 0 | 2 | 11 | 0 | 2 | 0 |

[1]IDs: codes for the truncated peptides

[2]"No peptide" controlwells subtracted

EAE
[DC2.4 or DC2.4/MOG196]
i.v.
[cLNs & Spleen]
FACS
Days 0
10
14 cLNs
Spleen
DC2.4
DC2.4/MOG196
6.07
3.52
13.2
3.98
Qa-1b/MOG196tet
CD8+

DC2.4
DC2.4/MOG196
% Qa-1b/MOG196 tet+ cells among CD8+ T cells
cLNs
Spleen 3.14
17.8
2.01
9.79
I-Ab/MOG35-49tet
CD8-

% I-Ab/MOG35-49 tet+ cells among CD8- T cells

DC2.4/MOG196
i.v.
Days 0 10 20
cLNs &
FACS ← Spleen

Gated on Qa-1b/MOG196tet+ cells
155
690
152
760
CD122
Ly49

Figure 8

| | |
|---|---|
| m | LVALIICYNWLHRRLAGQFL |
| r | LVALIICYNWLHRRLAGQFL |
| C Jacchus | LVALIICYNWLHRRLAGQFL |
| h | LVALIICYNWLHRRLAGQFL |

SEQUENCE LISTING

```
Sequence total quantity: 23
SEQ ID NO: 1           moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 1
IICYNWLHR                                                              9

SEQ ID NO: 2           moltype = AA  length = 6
FEATURE                Location/Qualifiers
REGION                 1..6
                       note = Description of Artificial Sequence: Synthetic peptide
source                 1..6
                       mol_type = protein
                       organism = synthetic construct
SEQUENCE: 2
IICYNW                                                                 6

SEQ ID NO: 3           moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 3
IICYNWL                                                                7

SEQ ID NO: 4           moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 4
IICYNWLH                                                               8

SEQ ID NO: 5           moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 5
IICYNWLHRR                                                             10
```

-continued

```
SEQ ID NO: 6            moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 6
IICYNWLHRR L                                                      11

SEQ ID NO: 7            moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 7
IICYNWLHRR LA                                                     12

SEQ ID NO: 8            moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 8
IICYNWLHRR LAG                                                    13

SEQ ID NO: 9            moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 9
IICYNWLHRR LAGQ                                                   14

SEQ ID NO: 10           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 10
IICYNWLHRR LAGQF                                                  15

SEQ ID NO: 11           moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 11
ICYNWLHRRL AGQF                                                   14

SEQ ID NO: 12           moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 12
CYNWLHRRLA GQF                                                    13

SEQ ID NO: 13           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 13
YNWLHRRLAG                                                        10
```

```
SEQ ID NO: 14           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 14
NWLHRRLAGQ F                                                        11

SEQ ID NO: 15           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 15
WLHRRLAGQF                                                          10

SEQ ID NO: 16           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 16
LHRRLAGQF                                                           9

SEQ ID NO: 17           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 17
HRRLAGQF                                                            8

SEQ ID NO: 18           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 18
RRLAGQF                                                             7

SEQ ID NO: 19           moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 19
RLAGQF                                                              6

SEQ ID NO: 20           moltype = AA  length = 20
FEATURE                 Location/Qualifiers
source                  1..20
                        mol_type = protein
                        organism = Mus sp.
SEQUENCE: 20
LVALIICYNW LHRRLAGQFL                                               20

SEQ ID NO: 21           moltype = AA  length = 20
FEATURE                 Location/Qualifiers
source                  1..20
                        mol_type = protein
                        organism = Rattus sp.
SEQUENCE: 21
LVALIICYNW LHRRLAGQFL                                               20

SEQ ID NO: 22           moltype = AA  length = 20
FEATURE                 Location/Qualifiers
```

-continued

```
source                  1..20
                        mol_type = protein
                        organism = Callithrix jacchus
SEQUENCE: 22
LVALIICYNW LHRRLAGQFL                                                       20

SEQ ID NO: 23           moltype = AA  length = 20
FEATURE                 Location/Qualifiers
source                  1..20
                        mol_type = protein
                        organism = Homo sapiens
SEQUENCE: 23
LVALIICYNW LHRRLAGQFL                                                       20
```

MYELIN OLIGODENDROCYTE GLYCOPROTEIN-SPECIFIC PEPTIDE FOR THE TREATMENT OR PREVENTION OF MULTIPLE SCLEROSIS

CROSS-REFERENCE TO RELATED APPLICATIONS

This application is a divisional of U.S. application Ser. No. 16/314,642, filed Dec. 31, 2018, titled "MYELIN OLIGODENDROCYTE GLYCOPROTEIN-SPECIFIC PEPTIDE FOR THE TREATMENT OR PREVENTION OF MULTIPLE SCLEROSIS," which is a national stage application of PCT/US17/40484, filed Jun. 30, 2017, titled "MYELIN OLIGODENDROCYTE GLYCOPROTEIN-SPECIFIC PEPTIDE FOR THE TREATMENT OR PREVENTION OF MULTIPLE SCLEROSIS," which claims priority to U.S. Provisional Patent Application No. 62/357,891, filed Jul. 1, 2016, titled "MYELIN OLIGODENDROCYTE GLYCOPROTEIN-SPECIFIC PEPTIDE FOR THE TREATMENT OR PREVENTION OF MULTIPLE SCLEROSIS," the entire content of which are incorporated by reference herein.

SEQUENCE LISTING

The instant application contains a Sequence Listing which has been submitted electronically in XML format and is hereby incorporated by reference in its entirety. Said XML copy, created on May 5, 2023, is named LLU 14-020_211_8.xml and is 28,924 bytes in size. The Sequence Listing does not extend beyond the scope of the specification, and does not add new matter.

TECHNICAL FIELD

The disclosure relates to compositions for the treatment or prevention of demyelinating disease.

BACKGROUND

Multiple sclerosis (MS) is a chronic and often debilitating disorder of the central nervous system (CNS). Data suggest that MS global prevalence and incidence rate are increasing (Melcon et al., *Journal of the Neurological Sciences,* 2014, 344:171-181). It is believed that MS is caused by attacks on the myelin sheath by one's own immune system.

Studies in MS autoimmune animal models (experimental autoimmune encephalomyelitis, or EAE) have led to a series of FDA-approved medications that have significantly slowed disease progression and improved patients' quality of life. However, currently available therapies still fail to halt autoimmune attacks in the CNS. There remains a need for methods of treating MS.

SUMMARY

According to one embodiment, a composition for treatment of multiple sclerosis is provided, the composition comprising: a peptide comprising a partial amino acid sequence of myelin oligodendrocyte glycoprotein, wherein the peptide activates a subset of immune cells. In some embodiments, a composition is provided wherein the activated immune cells comprise HLA-E-restricted regulatory $CD8^+$ T cells. In some embodiments, a composition is provided wherein the peptide comprises a MOG-specific MHC 1b epitope.

According to another embodiment, a method for treating multiple sclerosis is provided, the method comprising: administering a peptide comprising a partial amino acid sequence of myelin oligodendrocyte glycoprotein; and activating a subset of immune cells, wherein the immune cells comprise HLA-E-restricted regulatory $CD8^+$ T cells. In some embodiments, a method is provided wherein the peptide comprises a MOG-specific MHC 1b epitope.

In another aspect, compositions for the treatment or prevention of multiple sclerosis are provided. In some embodiments, the composition comprises an isolated peptide comprising a partial amino acid sequence of a myelin oligodendrocyte glycoprotein (MOG) protein, wherein the peptide activates regulatory T cells. In some embodiments, the composition comprises dendritic cells pulsed with a myelin oligodendrocyte glycoprotein (MOG) peptide that activates regulatory T cells.

In some embodiments, the peptide comprises a MOG-specific MHC1b epitope. In some embodiments, the peptide comprises a HLA-E epitope. In some embodiments, the peptide comprises the amino acid sequence IICYNWLHR (SEQ ID NO: 1). In some embodiments, the peptide consists of the amino acid sequence IICYNWLHR (SEQ ID NO: 1). In some embodiments, the peptide activates HLA-E-restricted regulatory $CD8^+$ T cells.

In some embodiments, the dendritic cells are derived from myelin-specific pathogenic autoimmune cells. In some embodiments, the dendritic cells are derived from monocytes.

In another aspect, methods of treating or preventing a demyelinating disease are provided. In some embodiments, the method comprises administering to a subject a composition as disclosed herein (e.g., an isolated peptide comprising a partial amino acid sequence of MOG (e.g., a peptide comprising or consisting of the amino acid sequence IICYNWLHR (SEQ ID NO: 1)), a composition comprising an isolated peptide comprising a partial amino acid sequence of MOG, or a composition comprising dendritic cells pulsed with an isolated peptide comprising a partial amino acid sequence of MOG). In some embodiments, methods of treating the demyelinating disease are provided. In some embodiments, methods of preventing or delaying the onset of the demyelinating disease are provided.

In some embodiments, the demyelinating disease is selected from the group consisting of multiple sclerosis, idiopathic inflammatory demyelinating disease, transverse myelitis, Devic's disease, progressive multifocal leukoencephalopathy, optic neuritis, leukoystrophy, Guillain-Barre syndrome, chronic inflammatory demyelinating polyneuropathy, autoimmune peripheral neuropathy, Charcot-Marie-Tooth disease, acute disseminated encephalomyelitis, adrenoleukodystrophy, adrenomyeloneuropathy, Leber's hereditary optic neuropathy, or HTLV-associated myelopathy. In some embodiments, the demyelinating disease is multiple sclerosis. In some embodiments, the composition is administered subcutaneously or intravenously.

In still another aspect, methods of treating multiple sclerosis are provided. In some embodiments, the method comprises administering to a subject having multiple sclerosis a composition comprising dendritic cells pulsed with a myelin oligodendrocyte glycoprotein (MOG) peptide that activates HLA-E-restricted regulatory $CD8^+$ T cells. In some embodiments, the peptide comprises or consists of the amino acid sequence IICYNWLHR (SEQ ID NO: 1). In some embodiments, the dendritic cells are derived from monocytes. In some embodiments, the dendritic cells are derived from monocytes that are autologous to the subject. In some embodiments, the dendritic cells are derived from monocytes that are allogeneic to the subject.

BRIEF DESCRIPTION OF THE DRAWINGS

FIG. 2A-2F. Recognition of multiple OLPs by the MOG_pool-reactive $CD8^+$ T cell lines depended on Qa-$1^b$. (A-D) MOG_pool-reactive $CD8^+$ T cell lines were generated as described in FIG. 1. The 59 individual OLPs were interrogated, using IFN-γ Enzyme-linked ImmunoSpot, for their ability to stimulate the MOG_pool-reactive $CD8^+$ T cell lines in the presence of either C1R or C1R.Qa-$1^b$ cells. (A) 96-well plate layout of the 59 individual OLPs. Numbers in the wells represent identification codes (IDs) for the 59 individual OLPs, i.e., 49-107 from N to C termini. (B)-(C) Responses of one representative MOG_pool-reactive $CD8^+$ T cell line to the 59 individual OLPs in the presence of either C1R (B) or C1R.Qa-$1^b$ (C) cells. Numbers represent spot forming cells (SFCs)/$10^6$ $CD8^+$ T cells. (D) Fold increases of SFCs/$10^6$ $CD8^+$ T cells in the wells that contained C1R.Qa-$1^b$ cells (C) as compared to C1R cells (B), i.e., numbers=(SFCs per $10^6$ $CD8^+$ T cells in C)/(SFCs per $10^6$ $CD8^+$ T cells in B). The highlighted boxes are the top three OLPs that stimulated unequivocal Qa-$1^b$-restricted $CD8^+$ T cell response. (E) Experimental design for assay in "F": $K^{b-/-}D^{b-/-}$ mice were immunized with OLP68, OLP96, or OLP105. $CD8^+$ T cells purified ten days later were stimulated with the corresponding peptides used for immunization. After one week of in vitro culture, the $CD8^+$ T cells were examined, using IFN-γ Enzyme-linked ImmunoSpot, for specific responses to the corresponding peptides in the presence of either C1R or C1R.Qa-$1^b$ cells. (F) Representative data from two independent experiments is shown.

FIG. 3 discloses SEQ ID NOS 2-4, 1 and 5-19, respectively, in order of appearance.

FIG. 8. $MOG_{196}$ sequence is conserved across species. The data show an alignment of the sequences surrounding $MOG_{196}$ in four different species. "m": mice (SEQ ID NO: 20); "r": rats (SEQ ID NO: 21); "*C jacchus": Callithrix jacchus* (SEQ ID NO: 22); "h": humans (SEQ ID NO: 23). The 9-mer peptide sequence IICYNWLHR (SEQ ID NO: 1) is underlined.

DETAILED DESCRIPTION

I. Introduction

Figure 1A:
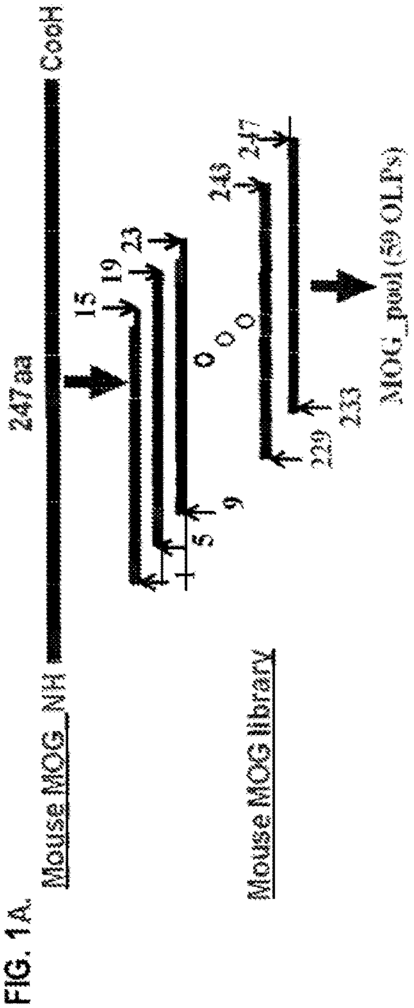
FIG. 1A-1C. Portion of $CD8^+$ T cells reactive to the pool of overlapping peptides (OLPs) covering the whole length of mouse MOG was Qa-$1^b$ restricted. (A) A schematic view of the mouse MOG OLP library. 15mer peptides across the whole length of mouse MOG (247 amino acids) and overlapped by 11 amino acids were synthesized. A pool of the 59 OLPs ("MOG_pool") at a concentration of 4.2 μg/ml for each peptide was then generated for stimulating $CD8^+$ T cells purified from $K^{b-/-}D^{b-/-}$ mice. (B) Experimental design for Enzyme-linked ImmunoSpot assay in "C": $CD8^+$ T cells purified from $K^{b-/-}D^{b-/-}$ mice were stimulated with the MOG_pool in vitro on a weekly basis. Before being stimulated each time, the $CD8^+$ T cells were monitored for response to the MOG_pool, using IFN-γ Enzyme-linked ImmunoSpot, in the presence of either C1R or C1R.Qa-$1^b$ cells as antigen presenting cells. (C) Enzyme-linked ImmunoSpot data on day 7 were shown and were representative of three independent experiments. The number at the upper left corner of each well is the absolute number of IFN-γ spot forming cells (SFCs) in the corresponding well (50,000 CD8 T cells/well).

Multiple sclerosis (MS) is a chronic and often debilitating disorder of the central nervous system (CNS). The ultimate goal of MS therapy is to specifically suppress the immune attacks on myelin sheath (a structure that protects nerve fibers in the CNS), while sparing global immune defense mechanisms (Steinman, *Mult Scler,* 2015, 21:1223-1238). However, currently available medications have not met this goal. Currently available therapies block one molecule that mediates the inflammatory attacks of myelin sheath in the CNS of MS patients. However, these blocked molecules are essential components in the immune system and participate in immune defense against infections and cancers. Consequently, normal immune defense mechanisms are attenuated and predictable side effects ensue. See, Clifford et al., *The Lancet Neurology,* 2010, 9:438-446; Linda et al., *The New England Journal of Medicine,* 2009, 361:1081-187. In principle, the adverse side effects associated with current therapies can be eliminated by antigen-specific therapy. See, e.g., Steinman, *Mult Scler,* 2015, 21:1223-1238; Lutterotti et al., *Journal of the Neurological Sciences,* 2008, 274:18-22. The goal of antigen-specific therapy is to specifically delete, anergize, or deviate myelin-specific pathogenic autoimmune cells that are responsible for MS. However, there is currently no FDA-approved antigen-specific therapy for MS.

Convincing evidence have shown that regulatory T (Treg) cells, a subset of immune cells, are important in preventing and/or arresting autoimmune attacks, e.g., the attacks on myelin sheath in MS patients. Recent studies suggest that HLA-E (a group of non-classical MHC Ib molecules)-restricted CD8$^+$ T cells, another subset of immune cells, are altered or deficient in MS patients. See, e.g., Ben-Nun et al., *J. Autoimmun.,* 2014, 54:33-50. The data therefore indicate that HLA-E-restricted CD8$^+$ T cells contain a subset of Treg (referred to herein as HLA-E-restricted CD8 Treg). HLA-E-restricted CD8$^+$ Treg may be involved in the prevention and/or therapy of MS, and this has been further supported by data gathered from studies of Qa-1-restricted CD8$^+$ Treg (the murine homologue of human HLA-E-restricted CD8$^+$ Treg). Qa-1-restricted CD8$^+$ Treg may maintain immune homeostasis under physiological condition. In addition, the CD8$^+$ Treg recognize specific peptides (also called regulatory Qa-1 epitopes) on and thereby target autoreactive T cells (i.e., the immune cell subset that causes autoimmune diseases).

At least two limitations may prevent current preclinical studies from clinical translation. The first limitation is that CD8$^+$ Treg activated by current strategies would mainly target autoreactive T cells in the peripheral lymphoid organs and may not have the capacity to specifically accumulate in the diseased CNS. Consequently, efficacy of current strategies may be compromised. The second limitation is that the CD8$^+$ Treg's targets in human, i.e., regulatory HLA-E epitopes expressed in autoreactive T cells, can be difficult to determine in patients. Therefore, current strategies are difficult to implement in clinics.

The present disclosure provides compositions and methods that overcome these limitations. As described herein, in one aspect a regulatory Qa-1 (HLA-E) epitope is disclosed. In some embodiments, the Qa-1 epitope is a "MOG-specific MHC1b epitope" (or "MSIBE"), that is specifically located in MOG, a protein located in myelin sheath that is attacked by the immune system in EAE. As described herein in the Examples section below, immunization with MSIBE but not non-MOG Qa-1 epitopes suppresses EAE. Additionally, data presented herein demonstrate that Qa-1-restricted CD8$^+$ Treg cells activated by MSIBE immunization are involved in efficient suppression of EAE. Because of MSIBE's unique location in MOG, an autoantigen that is the ultimate target of autoreactive T cells in EAE and in MS, Qa-1-restricted (or HLA-E-restricted) CD8$^+$ Treg activated by MSIBE may specifically accumulate at and arrest the autoimmune attacks on myelin sheath in EAE and in MS. Thus, in some embodiments, MSIBE can be used as a peptide vaccine for specific prevention and therapy of MS.

In some embodiments, a 9mer peptide (hereafter epitope) that is specifically located in myelin oligodendrocyte glycoprotein (MOG), a major autoantigen in multiple sclerosis (MS), is provided. In some embodiments, the epitope has the amino acid sequence IICYNWLHR (SEQ ID NO: 1). In some embodiments, the MSIBE epitope can be used for activating a subset of immune cells, specifically HLA-E (Qa-1 in mouse)-restricted regulatory CD8$^+$ T cells (also referred to herein as "HLA E(Qa-1)-restricted CD8$^+$ Treg") for the specific prevention and therapy of MS.

II. Definitions

The terminology used herein is for the purpose of describing particular embodiments only, and is not intended to be limiting, because the scope of the present invention will be limited only by the appended claims. Unless defined otherwise, all technical and scientific terms used herein have the same meaning as commonly understood by one of ordinary skill in the art to which this invention belongs. In this specification and in the claims that follow, reference will be made to a number of terms that shall be defined to have the following meanings unless a contrary intention is apparent. In some cases, terms with commonly understood meanings are defined herein for clarity and/or for ready reference, and the inclusion of such definitions herein should not be construed as representing a substantial difference over the definition of the term as generally understood in the art.

As used in this disclosure, except where the context requires otherwise, the method steps disclosed are not intended to be limiting nor are they intended to indicate that each step is essential to the method or that each step must occur in the order disclosed.

All numerical designations, e.g., pH, temperature, time, concentration, and molecular weight, including ranges, are approximations which are varied (+) or (−) by increments of 0.1 or 1.0, as appropriate. It is to be understood, although not always explicitly stated that all numerical designations are preceded by the term "about."

The singular forms "a," "an," and "the" include plural referents unless the context clearly dictates otherwise. Thus, for example, reference to "a compound" includes a plurality of compounds.

The term "comprising" is intended to mean that the compounds, compositions and methods include the recited elements, but not excluding others. "Consisting essentially of" when used to define compounds, compositions and methods, shall mean excluding other elements that would materially affect the basic and novel characteristics of the claimed invention. "Consisting of" shall mean excluding any element, step, or ingredient not specified in the claim. Embodiments defined by each of these transition terms are within the scope of this invention.

As used herein, "myelin oligodendrocyte glycoprotein" or "MOG" refers to a glycoprotein that is expressed on the oligodendrocyte cell surface and the outermost surface of myelin sheaths. In some embodiments, a MOG protein is a human MOG protein. Human MOG is known to have alternatively spliced transcript variants. Sequences for human MOG mRNA are set forth in, e.g., NCBI GenBank Accession Nos. NM_001008228.2, NM_001008229.2, NM_001170418.1, NM_002433.4, NM_206809.3, NM_206810.3, NM_206811.3, NM_206812.3, and NM_206814.5. Sequences for human MOG protein are set forth in, e.g., NCBI GenBank Accession Nos. NP_001008229.1, NP_001008230.1, NP_001163889.1, NP_002424.3, NP_996532.2, NP_996533.2, NP_996534.2, NP_996535.2, and NP_996537.3. In some embodiments, a MOG protein or peptide is a homolog or ortholog of a human sequence disclosed herein (e.g., a mouse, rat, cynomolgus monkey, or marmoset (*C. jacchus*) form of MOG or a peptide thereof). In some embodiments, a MOG protein is a mouse MOG protein. The sequence for mouse MOG protein is set forth in, e.g., NCBI GenBank Accession No. NP_034944.2.

As used herein, the term "MOG-specific MHC1b epitope" or "MSIBE" refers to an epitope in myelin oligodendrocyte glycoprotein (MOG), e.g., human MOG or mouse MOG, that binds to a non-classical major histocompatibility complex 1b (MHC1b) molecule. In some embodiments, the MHC1b molecule is the antigen HLA-E (in humans) or Qa-1 (in mice).

As used herein, the term "epitope" refers to an area or region of a protein that specifically binds to an antigen (e.g., a MHC1b molecule, e.g., HLA-E or Qa-1), and can include a few amino acids, e.g., 5, 6, 7, 8, 9, 10, 11 or more amino acids. In some embodiments, the epitope is comprised of consecutive amino acids of a protein (e.g., 5, 6, 7, 8, 9, 10, 11 or more consecutive amino acids). In some embodiments, the term "epitope" as used herein refers to a peptide (e.g., an isolated peptide) comprising or consisting of the area or region of the protein that specifically binds to the antigen.

As used herein, the term "specifically binds" refers to a molecule (e.g., a peptide) that binds to a target (e.g., an antigen) with greater affinity, greater avidity, and/or greater duration to that target in a sample than it binds to another non-target compound (e.g., a structurally different antigen). In some embodiments, the molecule (e.g., peptide) specifically binds to the target (e.g., antigen) with at least 3-fold greater affinity than other non-target compounds, e.g., at least 4-fold, at least 5-fold, at least 6-fold, at least 7-fold, at least 8-fold, at least 9-fold, or at least 10-fold greater affinity.

The term "isolated," as used herein with reference to a protein or peptide, denotes that the protein or peptide is essentially free of other cellular components with which it is associated in the natural state. It is preferably in a homogeneous state. Purity and homogeneity are typically determined using analytical chemistry techniques such as electrophoresis (e.g., polyacrylamide gel electrophoresis) or chromatography (e.g., high performance liquid chromatography). In some embodiments, an isolated protein or peptide is at least 85% pure, at least 90% pure, at least 95% pure, or at least 99% pure.

The term "demyelinating disease," as used herein, refers to a disease or condition of the nervous system characterized by damage to or loss of the myelin sheath of neurons. A demyelinating disease can be a disease affecting the central nervous system or a disease affecting the peripheral nervous system. Examples of demyelinating diseases include, but are not limited to, multiple sclerosis, idiopathic inflammatory demyelinating disease, transverse myelitis, Devic's disease, progressive multifocal leukoencephalopathy, optic neuritis, leukoystrophy, Guillain-Barre syndrome, chronic inflammatory demyelinating polyneuropathy, autoimmune peripheral neuropathy, Charcot-Marie-Tooth disease, acute disseminated encephalomyelitis, adrenoleukodystrophy, adrenomyeloneuropathy, Leber's hereditary optic neuropathy, or HTLV-associated myelopathy. In some embodiments, the demyelinating disease is multiple sclerosis.

As used herein, the term "subject" or "patient" refers to a human or a non-human mammal, e.g., a dog, a cat, a mouse, a rat, a cow, a sheep, a pig, a goat, or a non-human primate, or a bird, e.g., a chicken, or any other vertebrate or invertebrate animal.

As used herein, the terms "treatment," "treating," and "treat" refer to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already having a disease or condition.

As used herein, an "effective amount" or a "therapeutically effective amount" refers to an amount of a therapeutic agent that is effective to relieve, to some extent, or to reduce the likelihood of onset of, one or more symptoms of a disease or condition (e.g., multiple sclerosis) and includes curing the disease or condition. A prophylactically effective amount, as used herein, refers to an amount that is effective to prevent or delay the onset of one or more symptoms of a disease or condition (e.g., multiple sclerosis), or otherwise reduce the severity of said one or more symptoms, when administered to a subject who does not yet exhibit symptoms of a disease or condition, but who is susceptible to, or otherwise at risk of, a particular disease or condition. In some embodiments, for a given parameter, a therapeutically effective amount will show an increase of therapeutic effect of at least 5%, 10%, 15%, 20%, 25%, 40%, 50%, 60%, 75%, 80%, 90%, or at least 100%. Therapeutic efficacy can also be expressed as "fold" increase or decrease. For example, a therapeutically effective amount can have at least a 1.2-fold, 1.5-fold, 2-fold, 5-fold, or more effect over a control.

The terms "administer," "administered," or "administering," as used herein, refer to introducing an agent into a subject or patient, such as a human. As used herein, the terms encompass both direct administration, (e.g., self-administration or administration to a patient by a medical professional) and indirect administration (e.g., the act of prescribing a compound or composition to a subject).

As used herein, the term "pharmaceutical composition" refers to a composition suitable for administration to a subject. In general, a pharmaceutical composition is sterile, and preferably free of contaminants that are capable of eliciting an undesirable response with the subject. Pharmaceutical compositions can be designed for administration to subjects in need thereof via a number of different routes of administration, including oral, intravenous, buccal, rectal, parenteral, intraperitoneal, intradermal, intratracheal, intramuscular, subcutaneous, inhalational, and the like.

III. Compositions and Kits

In one aspect, compositions for treating or preventing a demyelinating disease (e.g., multiple sclerosis or EAE) are provided. In some embodiments, the composition comprises an isolated peptide comprising a partial amino acid sequence of a myelin oligodendrocyte glycoprotein (MOG) protein, wherein the peptide activates a subset of immune cells.

In some embodiments, the peptide comprises a MOG-specific MHC1b epitope. In some embodiments, the peptide comprises a HLA-E epitope (in humans) or a Qa-epitope (in mice). In some embodiments, the peptide comprises a portion of a MOG sequence of set forth in, e.g., NCBI GenBank Accession Nos. NP_001008229.1, NP_001008230.1, NP_001163889.1, NP_002424.3, NP_996532.2, NP_996533.2, NP_996534.2, NP_996535.2, or NP_996537.3, or a homolog thereof. In some embodiments, the peptide comprises about 7-25, about 7-20, about 7-15, about 8-25, about 8-20, about 8-15, about 9-25, about 9-20, about 9-15, or about 9-13 contiguous amino acids of a MOG sequence as described herein. In some embodiments, the peptide comprises at least about 7, at least about 8, or at least about 9 contiguous amino acids of a MOG sequence as described herein. In some embodiments, the peptide comprises up to about 25, up to about 20, up to about 15, up to about 12, or up to about 10 contiguous amino acids of a MOG sequence as described herein. In some embodiments, the peptide comprises a portion of a human MOG protein as described herein. In some embodiments, the peptide comprises a portion of a non-human MOG homolog. In some embodiments, the peptide comprises a portion of a mouse MOG protein as described herein. In some embodiments, the peptide comprises the amino acid sequence IICYNWLHR (SEQ ID NO: 1). In some embodiments, the peptide consists of the amino acid sequence IICYNWLHR (SEQ ID NO: 1). The amino acid sequence IICYNWLHR (SEQ ID NO: 1) is also referred to herein as "$MOG_{196-204}$" or "$MOG_{196}$", in reference to the region of the MOG protein from which the peptide is derived.

In some embodiments, the peptide activates regulatory T cells. In some embodiments, the peptide activates Qa-1-restricted or HLA-E-restricted regulatory $CD8^+$ T cells.

In some embodiments, methods of identifying a peptide that binds to Qa-1 or HLA-E and activates Qa-1-restricted or HLA-E-restricted regulatory $CD8^+$ T cells are provided. In some embodiments, the method comprises retrieving a myelin oligodendrocyte glycoprotein (MOG)-specific epitope (peptide) that binds to Qa-$1^b$, a non-classical MHCIb molecule. In some embodiments, the method comprises the use of an overlapping peptide (OLP) library of MOG peptide, such as an OLP library of murine MOG that contains 59 OLPs, which is described herein in the Examples section and referred to herein as "MOG_pool." In some embodiments, the method comprises the use of the cell line C1R, a human B lymphoblastoid cell line and/or C1R.Qa-$1^b$, a stable Qa-1transfectant of C1R cells. An OLP library can be used to generate reactive $CD8^+$ T cell lines, which can then be employed to screen individual OLPs in the OLP library and identify peptides that stimulate the reactive $CD8^+$ T cell lines in a Qa-$1^b$-restricted manner. In some embodiments, a Qa-$1^b$-restricted response is determined by an OLP-stimulated increased IFN-γ secretion in the reactive $CD8^+$ T cell lines in the presence of C1R.Qa-$1^b$ but not C1R cells.

In some embodiments, the methods of identifying a peptide that binds to Qa-1 or HLA-E and activates Qa-1-restricted or HLA-E-restricted regulatory $CD8^+$ T cells further comprise confirming whether the peptide binds to HLA-E, the human homolog of murine Qa-1. In some embodiments, the method comprises the use of a binding assay as described in the Examples section below and/or the use of a HLA-E-expressing cell line as described in the Examples section below (e.g., by incubating the peptide with the cell line 721.21-HLAE and using flow cytometry to determine whether HLA-E expression on the cell surface of 721.221-HLAE is upregulated after co-incubation with the peptide).

In some embodiments, the methods of identifying a peptide that binds to Qa-1 or HLA-E and activates Qa-1-restricted or HLA-E-restricted regulatory $CD8^+$ T cells further comprise confirming that MSIBE can bind to Qa-$1^b$ and activate MSIBE-specific Qa-$1^b$-restricted $CD8^+$ T cells in vitro. In some embodiments, the method comprises the use of a binding assay as described in the Examples section below (e.g., tetramer formation and detection of tetramer+ cells).

In some embodiments, the methods of identifying a peptide that binds to Qa-1 or HLA-E and activates Qa-1-restricted or HLA-E-restricted regulatory $CD8^+$ T cells further comprise confirming that the peptide can activate specific HLA-E-restricted $CD8^+$ Treg in vitro and thereby potentially suppress MS. In some embodiments, the method involves utilizing the peptide to activate HLA-E restricted $CD8^+$ Treg in vivo. In some embodiments, the method includes MSIBE, peripheral blood mononuclear cells (PBMCs), MSIBE/HLA-E tetramer, and human MOG-specific CD4$^+$ T cell lines. As a non-limiting example, CD8$^+$ T cells can be purified from peripheral blood mononuclear cells (PBMCs) of healthy control individuals, stimulated with peptide-pulsed autologous monocytes at weekly basis, and monitored for binding to HLA-E (e.g., via formation of a peptide/HLA-E tetramer). When peptide/HLA-E tetramer+ cells reach more than 50%, the CD8$^+$ T cell line is examined for its ability to specifically suppress proliferation of human MOG− but not control protein-specific CD4$^+$ T cells using a CFSE− dilution assay.

In some embodiments, the methods of identifying a peptide that binds to Qa-1 or HLA-E and activates Qa-1-restricted or HLA-E-restricted regulatory CD8$^+$ T cells further comprise confirming that immunization with the peptide can activate Qa-1$^b$-restricted CD8$^+$ T cells in vivo and suppress EAE. Methods of inducing EAE in mice and immunizing mice with peptides or dendritic cells pulsed with peptides are described in the Examples section below. In some embodiments, suppression of one or more clinical disease symptoms indicates that the peptide is a peptide that binds to Qa-1 or HLA-E and activates Qa-1-restricted or HLA-E-restricted regulatory CD8$^+$ T cells.

Peptide-Pulsed Dendritic Cells

In some embodiments, dendritic cells pulsed with a myelin oligodendrocyte glycoprotein (MOG) peptide that activates regulatory T cells are provided. In some embodiments, the peptide activates HLA-E-restricted or Qa-1-restricted regulatory CD8$^+$ T cells. In some embodiments, the peptide comprises a MOG-specific MHC1b epitope. In some embodiments, the peptide comprises a HLA-E epitope. In some embodiments, the peptide comprises the amino acid sequence IICYNWLHR (SEQ ID NO: 1). In some embodiments, the peptide consists of the amino acid sequence IICYNWLHR (SEQ ID NO: 1). Methods for peptide pulsing dendritic cells are described herein in the Examples section. Methods for peptide pulsing dendritic cells are also known in the art. See, e.g., O'Neill et al., *Methods Mol Med,* 2005, 109:97-112.

The dendritic cell can be obtained or derived from any suitable source. For example, the dendritic cell may be a bone marrow-derived dendritic cell, a cord blood-derived dendritic cell, or a peripheral blood-derived dendritic cell. In some embodiments, the dendritic cells are derived from monocytes. In some embodiments, the dendritic cells are derived from myelin-specific pathogenic autoimmune cells. Methods of generating dendritic cells are described herein in the Examples section. Methods of isolating and generating dendritic cells are also known in the art. See, e.g., Nair et al., *Curr Protoc Immnol,* 2012, doi: 10.1002/0471142735.im0732s99; Shen et al., *J. Immnol.,* 1997, 158: 2723-2730.

In some embodiments, the dendritic cells are immunogenic dendritic cells. In some embodiments, the dendritic cells are tolerogenic dendritic cells.

In some embodiments, the dendritic cell is an activated dendritic cell. In some embodiments, the dendritic cell is activated by stimulating the cell with a lipopolysaccharide (LPS) or with a cytokine (e.g., TNF-α).

In some embodiments, the dendritic cell is treated with an anti-proliferative agent. In some embodiments, the anti-proliferative agent is irradiation (e.g., gamma irradiation). In some embodiments, the anti-proliferative agent is a chemical compound (e.g., mitomycin C).

Pharmaceutical Compositions

In some embodiments, the composition comprises a peptide as described herein or a peptide-pulsed dendritic cell as described herein and further comprises a pharmaceutically acceptable carrier and/or excipient. Guidance for preparing formulations for use in the present invention is found in, for example, *Remington: The Science and Practice of Pharmacy,* 21st Edition, Philadelphia, PA, Lippincott Williams & Wilkins, 2005.

A pharmaceutically acceptable carrier includes any solvents, dispersion media, or coatings that are physiologically compatible and that preferably does not interfere with or otherwise inhibit the activity of the therapeutic agent. In some embodiments, the carrier is suitable for intravenous, intramuscular, oral, intraperitoneal, transdermal, topical, or subcutaneous administration. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers. Other pharmaceutically acceptable carriers and their formulations are well-known and generally described in, for example, *Remington: The Science and Practice of Pharmacy*, supra. Various pharmaceutically acceptable excipients are well-known in the art and can be found in, for example, Handbook of Pharmaceutical Excipients (7$^{th}$ edition, Rowe et al. (Eds.), Pharmaceutical Press, 2012).

In addition, various adjuvants such as are commonly used in the art may be included. Considerations for the inclusion of various components in pharmaceutical compositions are described, e.g., in *Goodman and Gilman's: The Pharmacological Basis of Therapeutics,* 12$^{th}$ edition, Brunton (Ed.), McGraw-Hill Education, 2011, which is incorporated herein by reference in its entirety.

The compositions described herein may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions include compositions that are administered by inhalation, and made using available methodologies. Depending upon the particular route of administration desired, a variety of pharmaceutically acceptable carriers well-known in the art may be used.

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell et al., "Compendium of Excipients for Parenteral Formulations," *FDA J Pharm Sci and Tech,* 1998, 52:238-311, and Nema et al., "Excipients and Their Role in Approved Injectable Products: Current Usage and Future Directions," *FDA J Pharm Sci and Tech,* 2011, 65:287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration.

In some embodiments, a composition as described herein is provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms can be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment.

Kits

In another aspect, kits comprising the peptides and/or dendritic cells disclosed herein are provided. In some embodiments, a kit further comprises instructional materials containing directions (i.e., protocols) for the practice of the methods of this invention (e.g., instructions for using the kit for treating a demyelinating disease, e.g., multiple sclerosis). While the instructional materials typically comprise written or printed materials they are not limited to such. Any medium capable of storing such instructions and communicating them to an end user is contemplated by this disclosure. Such media include, but are not limited to electronic storage media (e.g., magnetic discs, tapes, cartridges, chips), optical media (e.g., CD ROM), and the like. Such media may include addresses to internet sites that provide such instructional materials.

IV. Methods of Treating or Preventing Demyelinating Diseases

In another aspect, methods of treating or preventing a demyelinating disease are provided. In some embodiments, methods of treating a demyelinating disease are provided. In some embodiments, methods of preventing or delaying the onset of a demyelinating disease are provided. In some embodiments, the method comprises administering to a subject (e.g., a subject having a demyelinating disease or a subject at risk of having or suspected of having a demyelinating disease) a composition as described herein (e.g., a peptide comprising or consisting of a MOG-specific MHC1b epitope, a composition comprising an isolated peptide comprising or consisting of a MOG-specific MHC1b epitope, or a composition comprising dendritic cells pulsed with an isolated peptide comprising or consisting of a MOG-specific MHC1b epitope).

In some embodiments, the demyelinating disease is selected from the group consisting of multiple sclerosis, idiopathic inflammatory demyelinating disease, transverse myelitis, Devic's disease, progressive multifocal leukoencephalopathy, optic neuritis, leukoystrophy, Guillain-Barre syndrome, chronic inflammatory demyelinating polyneuropathy, autoimmune peripheral neuropathy, Charcot-Marie-Tooth disease, acute disseminated encephalomyelitis, adrenoleukodystrophy, adrenomyeloneuropathy, Leber's hereditary optic neuropathy, or HTLV-associated myelopathy. In some embodiments, the demyelinating disease is multiple sclerosis.

In some embodiments, the demyelinating disease is a disease characterized by the expression or overexpression of antibodies against MOG. In some embodiments, the demyelinating disease that expresses or overexpresses antibodies against MOG is multiple sclerosis, transverse myelitis, optic neuritis, or acute disseminated encephalomyelitis.

In some embodiments, the subject has multiple sclerosis (MS). There are several subtypes of MS, including relapsing-remitting multiple sclerosis (RRMS), secondary progressive multiple sclerosis (SPMS), primary progressive multiple sclerosis (PPMS), and progressive relapsing multiple sclerosis (PRMS). In some embodiments, the subject has RRMS. In some embodiments, the subject has SPMS. In some embodiments, the subject has PPMS. In some embodiments, the subject has PRMS. A subject may initially be diagnosed as having one subtype of MS (e.g., RRMS), and subsequently the subtype of MS afflicting the subject may convert to another subtype of MS (e.g., from RRMS to SPMS). It is contemplated that the therapeutic methods disclosed herein can be applied to treat a subject whose subtype of MS converts to another subtype of MS.

In some embodiments, a MOG peptide or dendritic cells pulsed with a myelin oligodendrocyte glycoprotein (MOG) peptide as described herein are used as a peptide vaccine for the prevention or treatment of MS or EAE. In some embodiments, the method comprises generating a vaccine comprising MSIBE and human dendritic cells (DCs). In some embodiments, the method of generating a vaccine comprises generating dendritic cells from monocytes that are autologous to the subject. In some embodiments, the method comprises generating dendritic cells from monocytes that are allogeneic to the subject. In some embodiments, the dendritic cells are generated in the presence of one or more cytokines (e.g., GM-CSF or interleukins, e.g., IL-4). In some embodiments, the dendritic cells are treated with an anti-proliferative agent. In some embodiments, the dendritic cells are pulsed with a peptide as described herein (e.g., MSIBE) and subsequently administered to a subject having MS. As a non-limiting exemplary embodiment, dendritic cells (e.g., $1\times10^6$ human DCs) can be generated from autologous monocytes in the presence of GM-CSF and IL-4, pulsed with a peptide as described herein (e.g., MSIBE), and injected subcutaneously or intravenously into MS patients.

In some embodiments, the method comprises optimizing immunization for prevention and therapy of MS or EAE. For example, in some embodiments, immunization with a MOG peptide or dendritic cells pulsed with a MOG peptide can be administered at varying amounts, or multiple immunizations can be performed, to improve the therapeutic response.

The route of administration of a peptide, dendritic cell, or composition as described herein (e.g., a peptide comprising or consisting of a MOG-specific MHC1b epitope, a composition comprising an isolated peptide comprising or consisting of a MOG-specific MHC1b epitope, or a composition comprising dendritic cells pulsed with an isolated peptide comprising or consisting of a MOG-specific MHC1b epitope, e.g., as described in Section III above) can be oral, intraperitoneal, transdermal, subcutaneous, intravenous, intramuscular, inhalational, topical, intralesional, rectal, intrabronchial, intralymphatic, intradermal, nasal, transmucosal, intestinal, ocular or otic delivery, or any other methods known in the art. In some embodiments, a peptide, dendritic cell, or composition as described herein is administered by intravenous injection or by subcutaneous injection. In some embodiments, a peptide, dendritic cell, or composition as described herein is administered systemically. In some embodiments, a peptide, dendritic cell, or composition as described herein is administered locally.

Dosages and desired concentrations of the peptides or dendritic cells of the disclosure may vary depending on the particular use envisioned. The determination of the appropriate dosage or route of administration is well within the skill of one in the art. Typically the amount administered to a subject is a therapeutically effective amount. In some embodiments, a therapeutically effective amount of a peptide, dendritic cell, or composition as described herein is an amount that prevents or reverses one or more symptoms of the disease (e.g., MS). In some embodiments, a therapeutically effective amount of a peptide, dendritic cell, or composition as described herein is administered about once per day, once per week, twice per week, once per month, or twice per month.

The peptides, dendritic cells, and compositions as described herein may be administered to a subject in need thereof for a predetermined time, an indefinite time, or until an endpoint is reached. In some embodiments, treatment is continued on a continuous daily or weekly basis for at least two to three months, six months, one year, or longer. In some embodiments, treatment is for at least 30 days, at least 60 days, at least 90 days, at least 120 days, at least 150 days, or at least 180 days. In some embodiments, treatment is continued for at least 6 months, at least 7 months, at least 8 months, at least 9 months, at least 10 months, at least 11 months, or at least one year. In some embodiments, treatment is continued for the rest of the patient's life or until administration is no longer effective to provide meaningful therapeutic benefit.

In some embodiments, the peptides, dendritic cells, and compositions as described herein are administered in combination with one or more additional agents (e.g., a therapeutic agent). In some embodiments, the two or more agents are administered at the same time or substantially the same time. In some embodiments, the two or more agents are administered sequentially. In some embodiments, the two or more agents are administered through the same route (e.g., intravenously). In some embodiments, the two or more agents are administered through different routes (e.g., the peptide, dendritic cell, or composition as described herein is administered intravenously and the additional agent is administered orally).

V. EXAMPLES

The following example are offered to illustrate, but not to limit, the claimed invention.

Example 1: Targeting Non-Classical Myelin Epitopes to Treat Experimental Autoimmune Encephalomyelitis Methods Mice: C57BL/6 (B6) and $K^{b-/-}d^{b-/-}$ mice were obtained from Taconic Farms and housed in a specific pathogen-free animal facility at the University of Texas at El Paso (UTEP) or Loma Linda University (LLU). All experiments were done in compliance with an Institutional Animal Care and Use Protocol approved by UTEP and/or LLU Animal Care and Use Committee.

Cell lines: C1R is a human B lymphoblastoid cell line. C1R.Qa-$1^b$ is a stable transfectant that constitutively expresses Qa-$1^b$. DC2.4 is a DC line generated from bone-marrow-derived DCs.

Reagents: Peptides used m this study were synthesized at Genemed Synthesis, Inc., San Antonio, TX.

IFN-γ Enzyme-linked Immunospot (EL/SPOT) assay: ELISPOT plates were coated with an anti-mouse IFN-γ mAb (5 μg/ml in PBS) at 4° C. overnight, blocked with culture medium for 2 hours at room temperature, and added with desired numbers of CD8+ T cells, peptides, and irradiated antigen-presenting cells (APCs). After cultured at 37° C. and 5% $CO_2$ for 16 hours, plates were incubated with a biotinylated anti-mouse IFN-γ mAb (2 μg/ml) for 2 hours followed by streptavidin-conjugated HRP (horseradish peroxidase) for 1 hour. Finally, plates were incubated with a substrate, monitored for spot development, and washed with distilled water when spots were fully developed. After air-drying, plates were analyzed on an ELISPOT plate reader for enumerating spots in each well.

In vitro refolding of a peptide with recombinant Qa-$1^b$ protein: Refolding of MOG196 with recombinant Qa-$1^b$ protein was performed in the NIH tetramer core facility (Emory University, Atlanta, GA) (Altman et al., Science, 1996, 274:94-96).

Induction of $MOG_{35-55}$-induced EAE: C57BL/6 mice were immunized subcutaneously with 200 μg $MOG_{35-55}$ emulsified in Incomplete Freund Adjuvant (IFA) supplemented with 250 μg heat-inactivated *Mycobacterium tuberculosis* H37Ra (Difeo Laboratories, Michigan, USA). On day 0 and 2, each mouse was administered 150 ng pertussis toxin (Calbiochem, Germany) intraperitoneally. Animals were then assessed for paralytic disease daily using the following scale: "O"=no paralysis, "I"=limp tail, "2"=limp tail and weak gait, "3"=hind limb paralysis, "4"=fore limb paralysis (animals were euthanized at or beyond stage "4").

Generation of bone marrow-derived dendritic cells (DCs): Bone marrow single cell suspensions ($1\times10^6$ cells/ml) containing 10 U/ml IL-4 and 100 U/ml GM-CSF were seeded into a 6-well plate (4 ml/well) and cultured at 37'C, 5% $CO_2$. On day 2, after non-adherent cells were carefully removed, plates were replenished with fresh media and cytokines. On day 4, non-adherent cells containing fresh media and cytokines were transferred into a new 6-well plate. On day 6, cells were replenished with fresh media and cytokines and stimulated with 0.1 μg/ml LPS overnight. On day 7, cells were collected for experiments.

Mitomycin C treatment of DCs and peptide pulsing: LPS activated DCs at the concentration of $5\times10^7$ cells/ml in PBC were treated by mitomycin C (50 μg/ml) for 20 minutes at 37° C. and 5% $CO_2$ (DC2.4 cells were treated for 30 minutes). The treated DCs were then washed for three times and adjusted to $5\times10^6$ cells/ml in serum-free medium containing 100 μg/ml $MOG_{196}$ or $HSP60_{P216}$ peptide. The cells were pulsed with the peptides for three to four hours at room temperature. After pulsing, the cells were washed once, reconstituted in PBS, and intravenously (or subcutaneously) injected into animals at 200 μl/mouse ($5\times10^5$ cells or $1\times10^6$ cells/mouse).

Multichromatic flow cytometry: Briefly, about $0.5\text{-}1\times10^6$ cells in a FACS buffer (PBS containing 1% FBS and 0.05% sodium azide) were stained with various fluorescence-conjugated antibodies specific for the desired cell surface proteins or with tetramers at 4'C for 30 min. The stained cells were washed twice in the FACS buffer before being analyzed on a BD FACSAria II.

Statistical analysis: All the statistical analyses were performed using One-Way or Two-Way ANOVA, followed by the SNK-q test or the Dunnett's Multiple Comparison test. A P-value less than 0.05 was considered statistically significant.

Results

A portion of $CD8^+$ T cells in the $CD8^+$ T cell lines reactive to the pool of overlapping peptides (OLPs) covering the whole length of mouse MOG was Qa-$1^b$ restricted. Current data suggest that Qa-1-restricted $CD8^+$ Treg cells can target pathogenic autoimmune cells (Jiang et al., *Immunity,* 1995, 2:185-194) and suppress EAE, an animal model of human MS. In this case, the $CD8^+$ T cells achieve the targeting by recognizing regulatory Qa-1 epitopes that are expressed in the myelin-specific pathogenic autoimmune cells (Tang et al., *J. Immunol.,* 2006, 177:7645-7655; Wu et al., *Proc Natl. Acad Sci USA,* 2009, 106:534-549; Panoutsakopoulou et al., *J. Clin Invest,* 2004, 113:1218-1224). These regulatory Qa-1 epitopes have been difficult to define in humans because pathogenic autoimmune cells by themselves are hard to determine in MS patients. This obstacle had previously prevented further clinical translation of the Qa-1-restricted $CD8^+$ Treg cells.

Figure 1B:
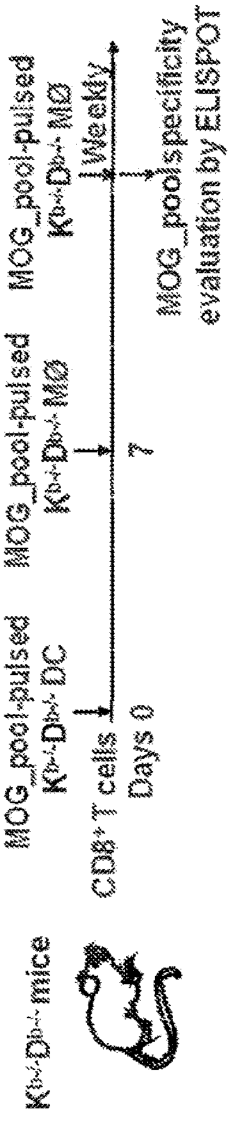
Figure 1C:
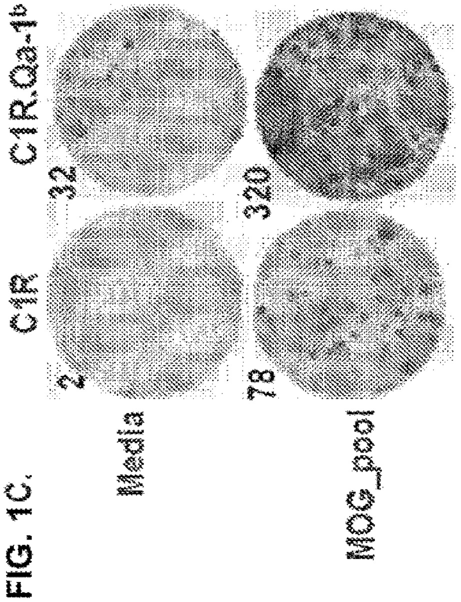

Pathogenic autoimmune cells in EAE and MS mainly attack myelin sheath. It was investigated whether Qa-1-restricted $CD8^+$ Treg cells could specifically target myelin sheath as well, and to determine if regulatory Qa-$1^b$ epitopes which are the targets of Qa-1-restricted $CD8^+$ Treg cells were present in mouse MOG since MOG is one of the myelin proteins in myelin sheath. In order to map potential Qa-$1^b$ epitopes in mouse MOG, a 15mer OLP library that covered the whole length of mouse MOG (247 amino acids) was generated from N- to C-termini. All of the OLPs in this library were 15 amino acids in length and overlapped by 11 amino acids. Hence the OLP library contained 59 OLPs in total (FIG. 1A). A pool of the 59 OLPs (MOG_pool), which contained a final concentration of 4.2 μg/ml for each individual peptide, was used to stimulate $CD8^+$ T cells purified from $K^{b-/-}d^{b-/-}$ mice for generating MOG_pool-reactive $CD8^+$ T cell lines in vitro. Here, $CD8^+$ T cells that were purified from $K^{b-/-}d^{b-/-}$ mice were utilized because $CD8^+$ T cells in these mice were restricted mostly by non-classical MHC $1^b$ molecules including Qa-$1^b$. During in vitro stimulations, $CD8^+$ T cell lines were monitored weekly for response, using IFN-γ Enzyme-linked ImmunoSpot, to the MOG_pool in the presence of either C1R or C1R.Qa-$1^b$ cells. The data showed that most $CD8^+$ T cell lines that were generated specifically responded to the MOG_pool in the presence of both C1R and C1R.Qa-$1^b$ cells (FIG. 1B and FIG. 1C). However, response to the MOG_pool was much stronger when C1R.Qa-$1^b$ cells were present. The data therefore suggested that portion of the $CD8^+$ T cells in the lines responded to the MOG_pool in a Qa-$1^b$-dependent (or Qa-1-restricted) manner.

Figure 2E:
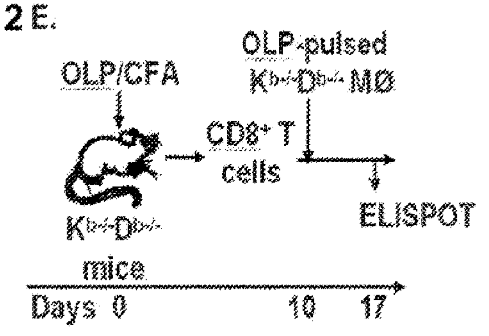
Figure 2F:
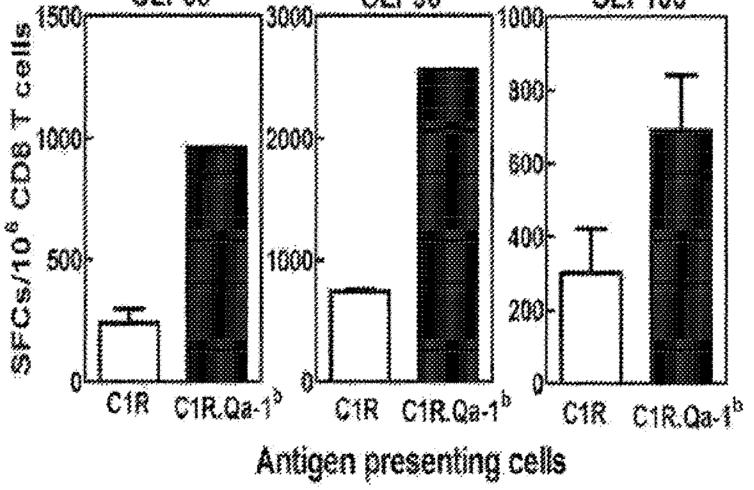

Recognition of multiple OLPs by the MOG_pool-reactive $CD8^+$ T cell lines depended on Qa-$1^b$. Next the question of which individual OLPs in the MOG_pool were recognized by the MOG_pool-reactive $CD8^+$ T cell lines in a Qa-$1^b$-restricted manner was investigated. Thus, the 59 individual OLPs were interrogated individually for their ability to stimulate the MOG_pool-reactive $CD8^+$ T cell lines in the presence of either C1R or C1R.Qa-$1^b$ cells as antigen-presenting cells (FIG. 2). Data showed that most OLPs provided stronger stimulation of the MOG_pool-reactive $CD8^+$ T cell lines in the presence of C1R.Qa-1b cells as compared to C1R cells (FIGS. 2B-D). However, only three OLPs, i.e., OLP68, OLP96, and OLP105, consistently stimulated the $CD8^+$ T cell lines in a Qa-$1^b$-restricted manner. A detailed analysis of these three OLPs was performed. Accordingly, $K^{b-/-}d^{b-/-}$ mice were immunized individually with the OLP68, OLP96, or OLP105. Ten days later, $CD8^+$ T cells were purified from draining lymph nodes and stimulated with corresponding peptides used for immunization. One week later, the $CD8^+$ T cells were examined for response, using IFN-γ Enzyme-linked ImmunoSpot, to the corresponding peptides in the presence of either C1R or C1R.Qa-$1^b$ cells. The data showed that all three OLPs stimulated $CD8^+$ T cells in a Qa-$1^b$-restricted manner (FIGS. 2E and 2F), suggesting that all three OLPs contained Qa-$1^b$ epitopes.

Figure 3:
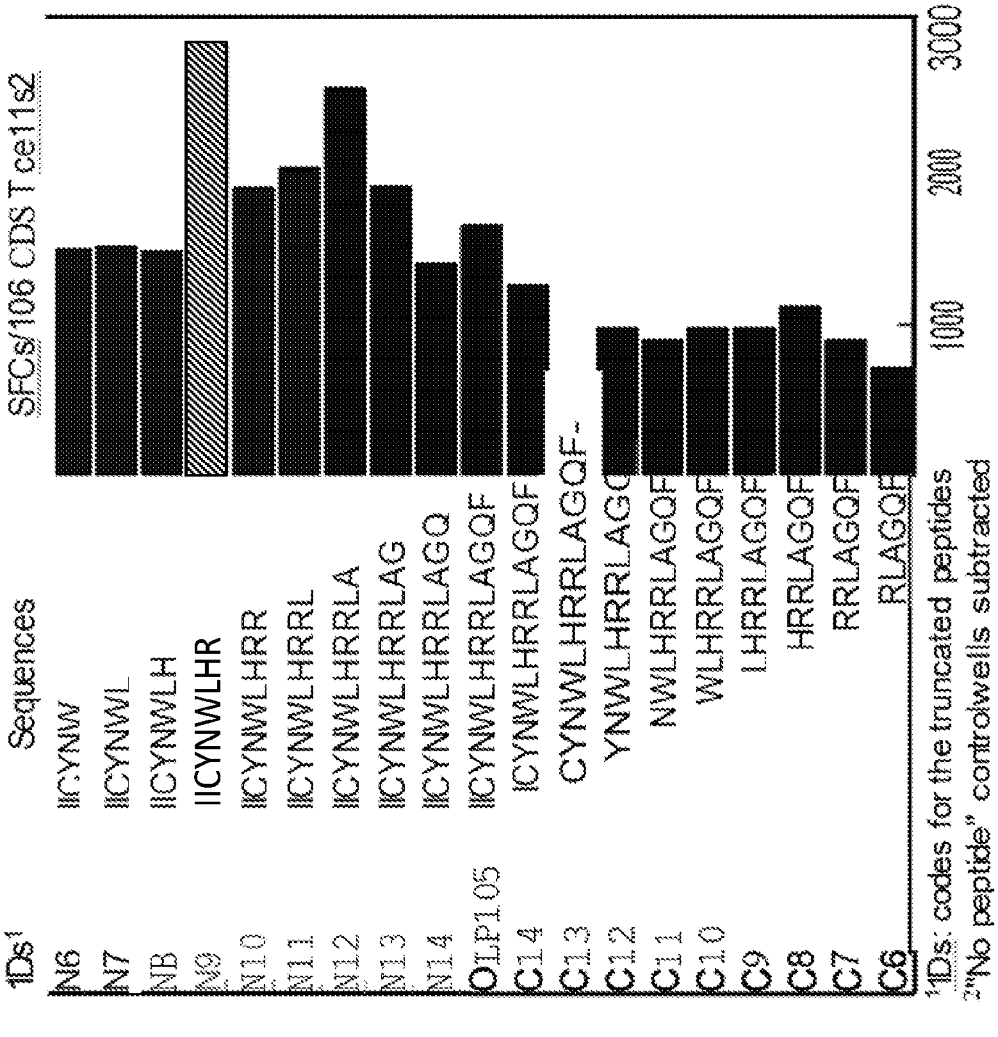
FIG. 3. Fine mapping of the minimal and optimal Qa-1b epitope in OLP105. Progressively N- and C-terminally truncated OLP105 peptides were synthesized and interrogated for their ability to stimulate, using IFN-γ Enzyme-linked ImmunoSpot, an OLP105-reactive CD8+ T cell line in the presence of C1R. Qa-1b cells. IDs and sequences of the truncated peptides are shown in the left and middle panels, respectively. Corresponding bars in the right panel show IFN-γ spot-forming cells (SFCs) per 106 $CD8^+$ T cells in response to corresponding peptides. Highlighted bar and sequence displayed the highest response and stimulating peptide sequence respectively, demonstrating that sequence of the optimal and minimal epitope in OLP105 was IICYNWLHR (SEQ ID NO: 1), i.e., MOG196-204 (also referred to herein as MOG196). The data was representative of four independent experiments.

$MOG_{196\text{-}204}$ ("$MOG_{196}$") was the minimal and optimal Qa-$1^b$ epitope in OLP105. Since OLP stimulated, in most assays, the highest number of SFCs (spot-forming cells)/106 $CD8^+$ T cells in the MOG_pool-reactive $CD8^+$ T cell lines in the presence of C1R.Qa-$1^b$ cells, the minimal and optimal Qa-$1^b$ epitope in this OLP was analyzed. Thus, progressively N- and C-terminally truncated peptides of OLP105 down to 6mers were synthesized because MHC I molecules can present epitopes of 7-10mers. These truncated peptides and the original OLP105 were then examined for their ability to stimulate, using IFN-γ Enzyme-linked ImmunoSpot, an OLP105-reactive $CD8^+$ T cell line in the presence of C1R.Qa-$1^b$ cells. Our data demonstrated that a 9mer peptide, IICYNWLHR (SEQ ID NO: 1), was the minimal and optimal epitope in OLP105 (FIG. 3).

Figure 4A:
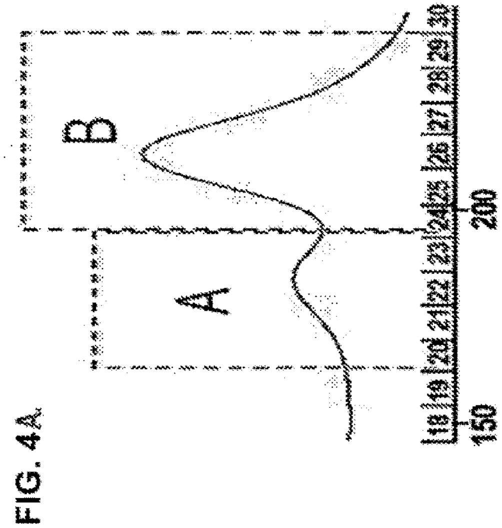
FIG. 4A-4D. $MOG_{196}$ can bind to Qa-$1^b$ and stimulate $MOG_{196}$-specific Qa-$1^b$-restricted $CD8^+$ T cells. (A) $MOG_{196}$ was incubated with recombinant Qa-$1^b$ and β2 microglobulin in a protein refolding buffer at 10° C. under gentle agitation (60 rpm) for four days. The solution was separated by a size exclusion column. Peak "A" and "B" represented typical non-specific protein aggregates and correctly refolded $MOG_{196}$/Qa-$1^b$ monomer, respectively. (B) Monomers in peak B of panel "A" were further analyzed by an anion exchange chromatography. (C) Proteins in peaks "A", "B1", and "B2" were biotinylated and portions of the biotinylated proteins were incubated with streptavidin (SA) to examine formation of tetramers. The biotinylated proteins and corresponding tetramers were analyzed in a non-denature protein gel. Arrows show protein bands for $MOG_{196}$/Qa-$1^b$ monomers. "–": without SA; "+": with SA; "pk A": peak A; "pk B1": peak B1; "pk B2" " peak B2; "Std": a protein standard. (D) $CD8^+$ T cells were purified from naïve C57Bl/6 (B6) mice, individually stimulated weekly with untreated (no peptide) or $MOG_{196}$-pulsed, either B6 (upper panels) or $K^{b-/-}D^{b-/-}$ (lower panels) macrophages. The $CD8^+$ T cells were analyzed for binding to Qa-$1^b$/$MOG_{196}$ tetramer at days 0, 7, and 14. One representative data on day 14 from four individual experiments was shown.
Figure 4B:
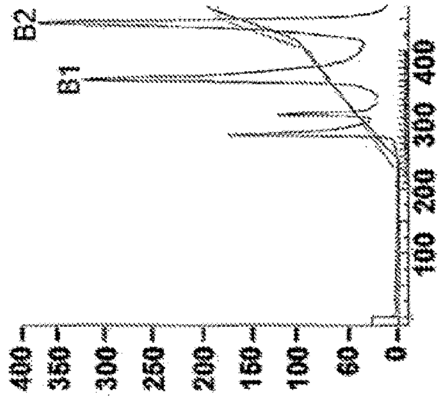
Figure 4C:
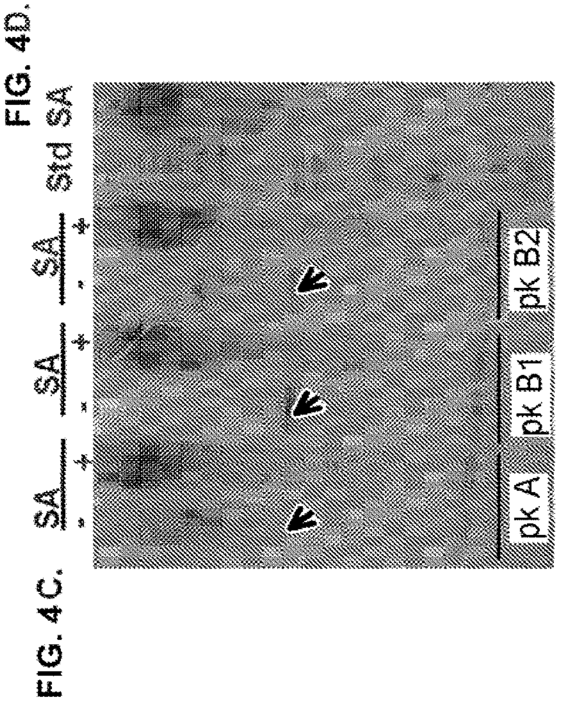

$MOG_{196}$ binds to Qa-$1^b$ and activates $MOG_{196}$—specific Qa-$1^b$—restricted $CD8^+$ T cells in vitro. To further confirm that $MOG_{196}$ was a Qa-$1^b$ epitope, we next asked whether $MOG_{196}$could bind to Qa-$1^b$ by addressing whether this 9mer peptide could successfully refold with recombinant Qa-$1^b$ protein in vitro. Thus, $MOG_{196}$ was incubated with recombinant Qa-1b protein and β2m at 10° C. for four days. The resulting solution was analyzed in a size exclusion column and displayed a distinct protein peak (FIG. 4A, peak B), suggesting formation of $MOG_{196}$/Qa-$1^b$/β2m monomer. When the monomer was further analyzed in an anion exchange column, the monomer displayed two protein peaks (FIG. 4B, peak B1 and B2). To further address potential reasons for the two protein peaks in the anion exchange column, proteins in peaks A, B1, and B2 were biotinylated. Portions of the biotinylated proteins were incubated with streptavidin that was able to bind four biotinylated proteins to form tetramers. Subsequently, the biotinylated proteins and streptavidin-conjugated tetramers were analyzed in a non-denature protein gel. Data showed that biotinylated proteins in peak A did not show any distinct protein band (FIG. 4C, lane 1), supporting that this peak contained mainly non-specific protein aggregates. In contrast, biotinylated proteins in peak B1 displayed a single protein band (FIG. 4C, lane 3), indicating correct formation of $MOG_{196}$/Qa-$1^b$/β2m monomer. Interestingly, biotinylated proteins in peak B2 exhibited two protein bands (FIG. 4C, lane 5), suggesting that some proteins in this peak were not correctly refolded. Furthermore, addition of streptavidin successfully conjugated biotinylated proteins in peak B1 and B2 into tetramers (FIG. 4C, lanes 4 and 6). The data therefore demonstrated that $MOG_{196}$ could bind to Qa-$1^b$.

Figure 4D:
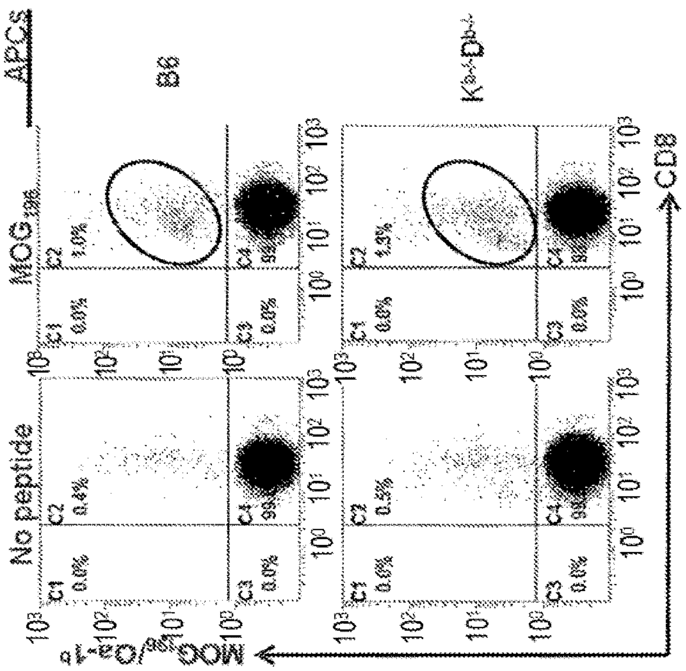

To investigate whether $MOG_{196}$ could be presented by antigen-presenting cells to activate $MOG_{196}$—specific Qa-$1^b$—restricted $CD8^+$ T cells, CD8+ T cells purified from C57Bl/6 mice were stimulated in vitro weekly by $MOG_{196}$-pulsed antigen-presenting cells derived from either $K^{b-/-}d^{b-/-}$ or C57Bl/6 mice. Data demonstrated that, beginning on day 14 after in vitro re-stimulation, Qa-$1^b$/$MOG_{196}$ tetramer+ cells could be detected in the $CD8^+$ T cell lines (FIG. 4D), indicating successful activation of $MOG_{196}$—specific Qa-$1^b$—restricted $CD8^+$ T cells. In addition, antigen-presenting cells derived from both $K^{b-/-}d^{b-/-}$ and C57Bl/6 mice were able to present $MOG_{196}$ to activate $MOG_{196}$—specific Qa-$1^b$—restricted $CD8^+$ T cells in vitro (FIG. 4D).

Figure 5A:
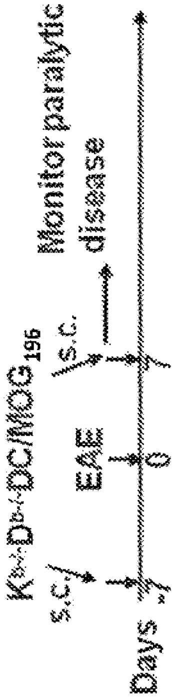
FIG. 5A-5D. Immunization with $MOG_{196}$-pulsed DCs suppressed $MOG_{35-55}$-induced EAE. (A) Experimental design for "B": C57BL/6 mice were immunized with $MOG_{35-55}$ for EAE. One week before and after the EAE induction, the animals received one of the following subcutaneous treatments: 1) no treatment (No Tx); 2) $1\times10^6$ Qdm-pulsed $K^{b-/-}D^{b-/-}$ DCs (DC/Qdm); 3) $1\times10^6$ $MOG_{196}$-pulsed $K^{b-/-}D^{b-/-}$ DCs (DC/$MOG_{196}$). The mice were then monitored for paralytic disease daily. (B) Daily mean disease score was shown. N=5. *$P<0.05$; $P<0.01$; *$P<0.001$. Two-way ANOVA test. (C) Experimental design for "D": C57BL/6 mice were immunized with $MOG_{35-55}$ for EAE on day 0. At days –3, 2, and 7, animals were immunized with $1\times10^6$ B6 DCs pulsed with Qdm (DC/Qdm), $HSP60_{p216}$ (DC/$HSP60_{p216}$), or $MOG_{196}$ (DC/$MOG_{196}$). The animals were then monitored for paralytic disease daily. (D) Daily mean disease score was shown. N=5. *$P<0.05$. Two-way ANOVA test. Concentration of peptides used for pulsing the DCs was 10 μg/ml.
Figure 5C:
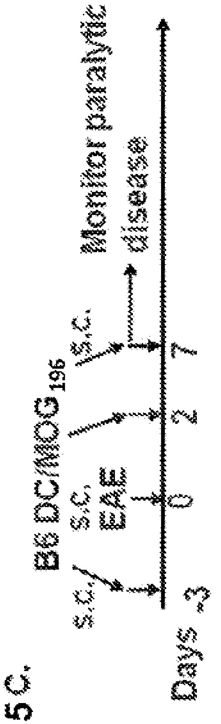
Figure 5B:
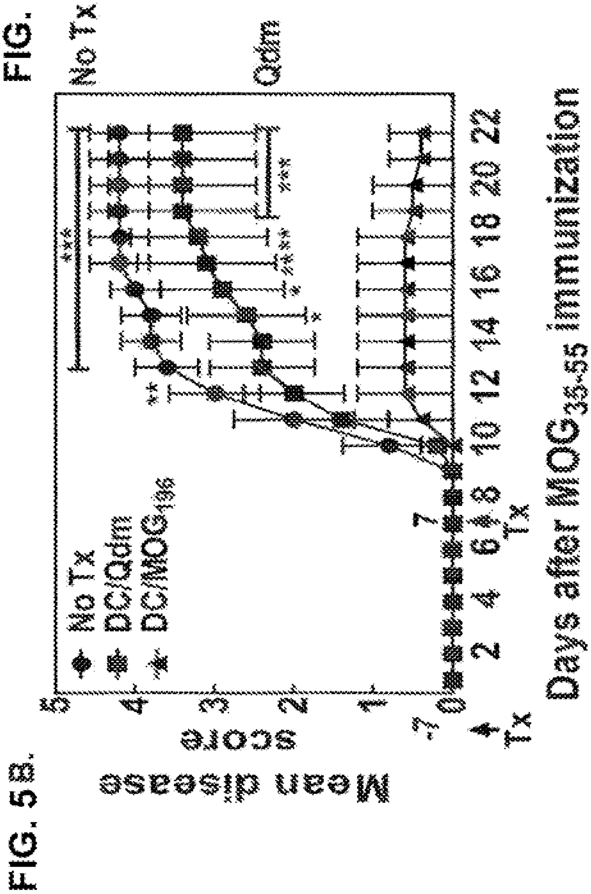

Vaccination with $MOG_{196}$-pulsed DCs suppressed $MOG_{35-55}$-induced EAE. To address whether $MOG_{196}$ is a biologically relevant Qa-$1^b$ epitope, an investigation was performed to determine if immunization with the epitope-pulsed DCs ameliorated $MOG_{35-55}$ EAE. Thus, C57Bl/6 (B6) mice were immunized with $MOG_{196}$-pulsed $K^{b-/-}d^{b-/-}$ DCs one week before and one week after the EAE induction. The data clearly showed that immunization with $MOG_{196}$ but not Qdm-pulsed $K^{b-/-}d^{b-/-}$ DCs significantly ameliorated the paralytic disease (FIGS. 5A-5B and Table 1).

TABLE 1

Vaccination with $MOG_{196}$-pulsed $K^{b-/-}D^{b-/-}$ dendritic cells suppressed $MOG_{35-55}$ induced experimental autoimmune encephalomyelitis

| Treatments | # of animals with disease/# of total animals (peak scores of individual animals) | Mean days of disease onset | Mean maximal disease score |
|---|---|---|---|
| No Tx[1] | 5/5 (4, 5, 4, 5, 4) | 10.8 ± 0.8 | 4.4 ± 0.5 |
| DCs/Qdm[2] | 4/5 (5, 5, 4, 0, 3) | 11.0 ± 0.8 | 3.4 ± 2.1 |
| DCs/MOG196[3] | 1/5 (0, 0, 0, 0, 3) | 11 ± 0.0 | 0.6 ± 1.3 |

Figure 5D:
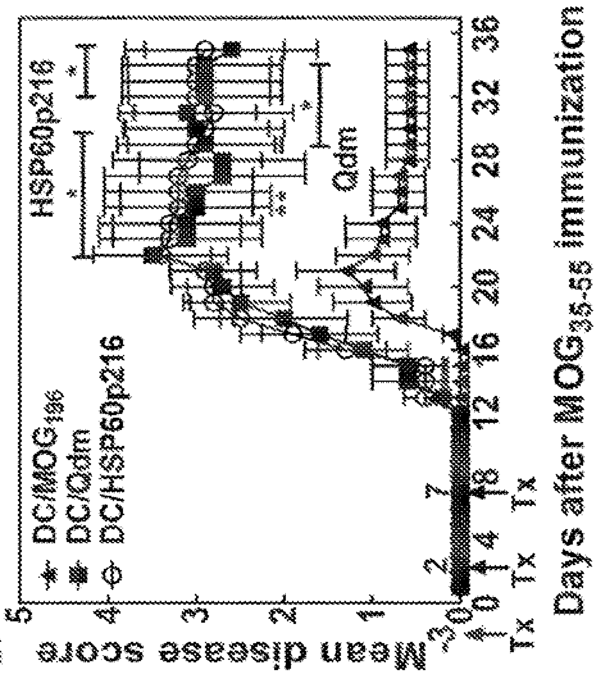

[1]No treatment
[2]Qdm-pulsed $K^{b-/-}D^{b-/-}$ dendritic cells
[3]$MOG_{196}$-pulsed $K^{b-/-}D^{b-/-}$ dendritic cells To evaluate the potential for wild-type DCs to ameliorate EAE, B6 mice were vaccinated with $MOG_{196}$-pulsed B6 DCs on days −3, 2, and 7. On day 0, mice were immunized with $MOG_{35-55}$ for EAE. The data again showed that vaccination with wild-type DCs pulsed with $MOG_{196}$, but not Qdm or $HSP60_{p216}$, significantly suppressed paralytic disease (FIGS. 5C-5D and Table 2).

TABLE 2

Vaccination with $MOG_{196}$-pulsed C57Bl/6 dendritic cells suppressed $MOG_{35-55}$ induced experimental autoimmune encephalomyelitis

| Treatments | # of animals with disease/# of total animals (peak scores of individual animals) | Mean days of disease onset | Mean maximal disease score |
|---|---|---|---|
| DCs/$HSP60_{p216}$[1] | 5/5 (3.5, 3.5, 3.5, 2.5, 2) | 14.2 ± 1.0 | 3.1 ± 0.3 |
| DCs/Qdm[2] | 5/5 (3.5, 3.5, 3.5, 2.5, 2) | 15 ± 1.1 | 3.2 ± 0.3 |
| DCs/MOG196[3] | 3/5 (2.5, 2.5, 1.5, 0, 0) | 16.7 ± 0.3 | 1.3 ± 0.6 |

[1]$HSP60_{p216}$-pulsed C57Bl/6 dendritic cells
[2]Qdm-pulsed C57Bl/6 dendritic cells
[3]$MOG_{196}$-pulsed C57Bl/6 dendritic cells Therefore, this epitope may be essential in maintaining immune homeostasis in the central nervous system (CNS).

Figure 6A:
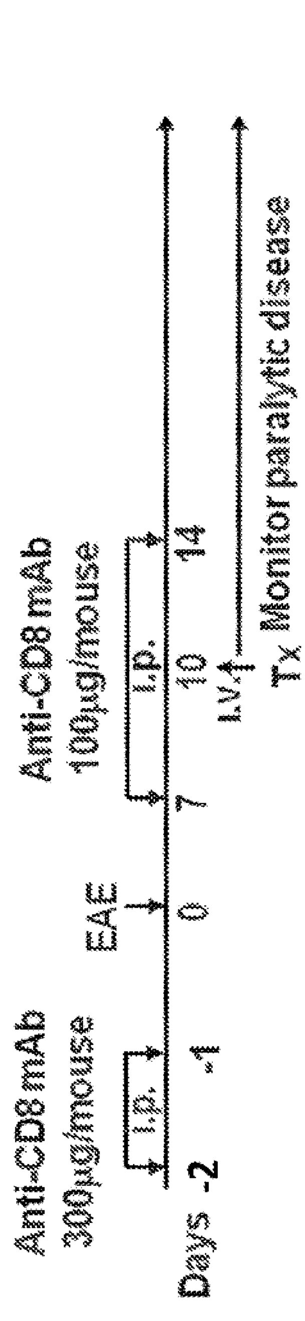
FIG. 6A-6B. Immunization with $MOG_{196}$-pulsed DCs suppressed ongoing $MOG_{35-55}$-induced EAE, which was dependent on $CD8^+$ T cells. (A) Experimental design for "B": C57BL/6 mice were immunized with $MOG_{35-55}$ for EAE on day 0. In one group, the animals were intraperitoneally injected with a monoclonal depleting anti-CD8 antibody (mAb) at days –2, –1, 7, and 14. At day 10, animals received either no treatment (No Tx) or one intravenous injection of mitomycin C-treated C57BL/6 DCs pulsed with $MOG_{196}$ (DC/$MOG_{196}$). Paralytic disease was monitored daily. (B) Daily mean disease score was shown. N=5 (one animal that died from EAE before antibody treatment was excluded from this analysis). *$P<0.05$; $P<0.01$; *$P<0.001$. Two-way ANOVA test. Data shown were representative of two independent experiments.
Figure 6B:
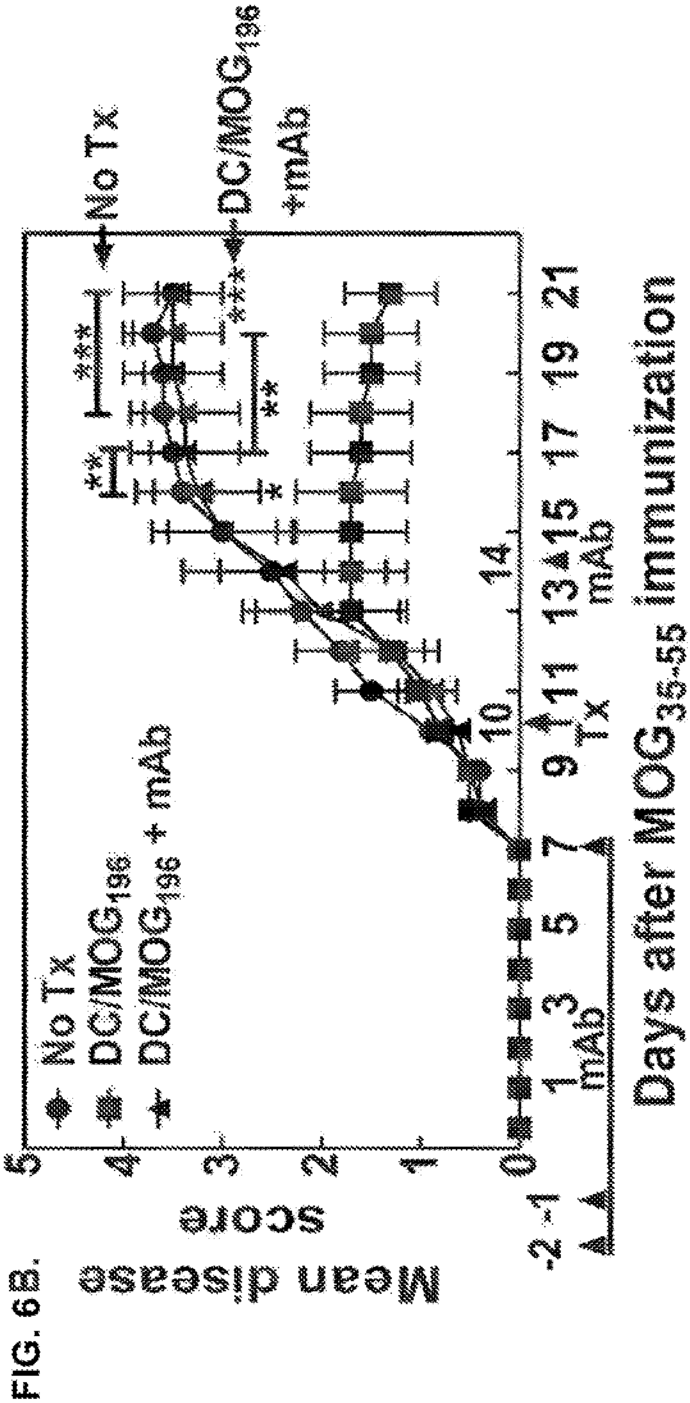

Vaccination with $MOG_{196}$-pulsed DCs suppressed ongoing $MOG_{35-55}$ EAE, which was dependent on $CD8^+$ T cells. Next, it was investigated whether immunization with the $MOG_{196}$ pulsed mature B6 DCs could suppress ongoing EAE and whether the disease suppression depended on $CD8^+$ T cells. Hence, C57Bl/6 mice were immunized with $MOG_{35-55}$ for EAE on day 0. In one group, the animals received an intra-peritoneal injection of a monoclonal anti-CD8 antibody at days −2, −1, 7 and 14 to deplete $CD8^+$ T cells. At day 10, animals received no treatment or one intravenous injection of $5\times10^5$ $MOG_{196}$-pulsed B6 DCs. The data showed that, as compared to no treatment, one intravenous injection of $5\times10^5$ $MOG_{196}$-pulsed B6 DCs robustly suppressed the ongoing paralytic disease (FIGS. 6A-6B and Table 3).

TABLE 3

Suppression of ongoing $MOG_{35-55}$ induced experimental autoimmune encephalomyelitis by $MOG_{196}$ immunization was dependent on CD8+ T cells

| Treatments | # of animals with disease/# of total animals (peak scores of individual animals) | Mean days of disease onset | Mean maximal disease score |
|---|---|---|---|
| No Tx[1] | 5/5 (3.5, 4, 4, 4, 3) | 8.4 ± 0.9 | 3.7 ± 0.4 |
| DCs/Qdm[2] | 5/5 (3, 1.5, 3, 0.5, 0.5) | 8 ± 0 | 1.7 ± 1.3 |
| DCs/MOG196[3] | 4/5 (3, 5, 3, 3)[4] | 8.3 ± 0.5 | 3.5 ± 1 |

[1]No treatment
[2]$MOG_{196}$-pulsed C57Bl/6 dendritic cells
[3]$MOG_{196}$-pulsed C57Bl/6 dendritic cells + anti-CD8 mAb
[4]One animal that died before treatment was excluded from this analysis.

Depletion of $CD8^+$ T cells abrogated the protective effect of the DC/$MOG_{196}$ Therefore, the data demonstrated that suppression of ongoing EAE by the $MOG_{196}$-pulsed DC was dependent on $CD8^+$ T cells.

Figures 7A, 7B, 7C, 7D, 7E, 7F, 7G:
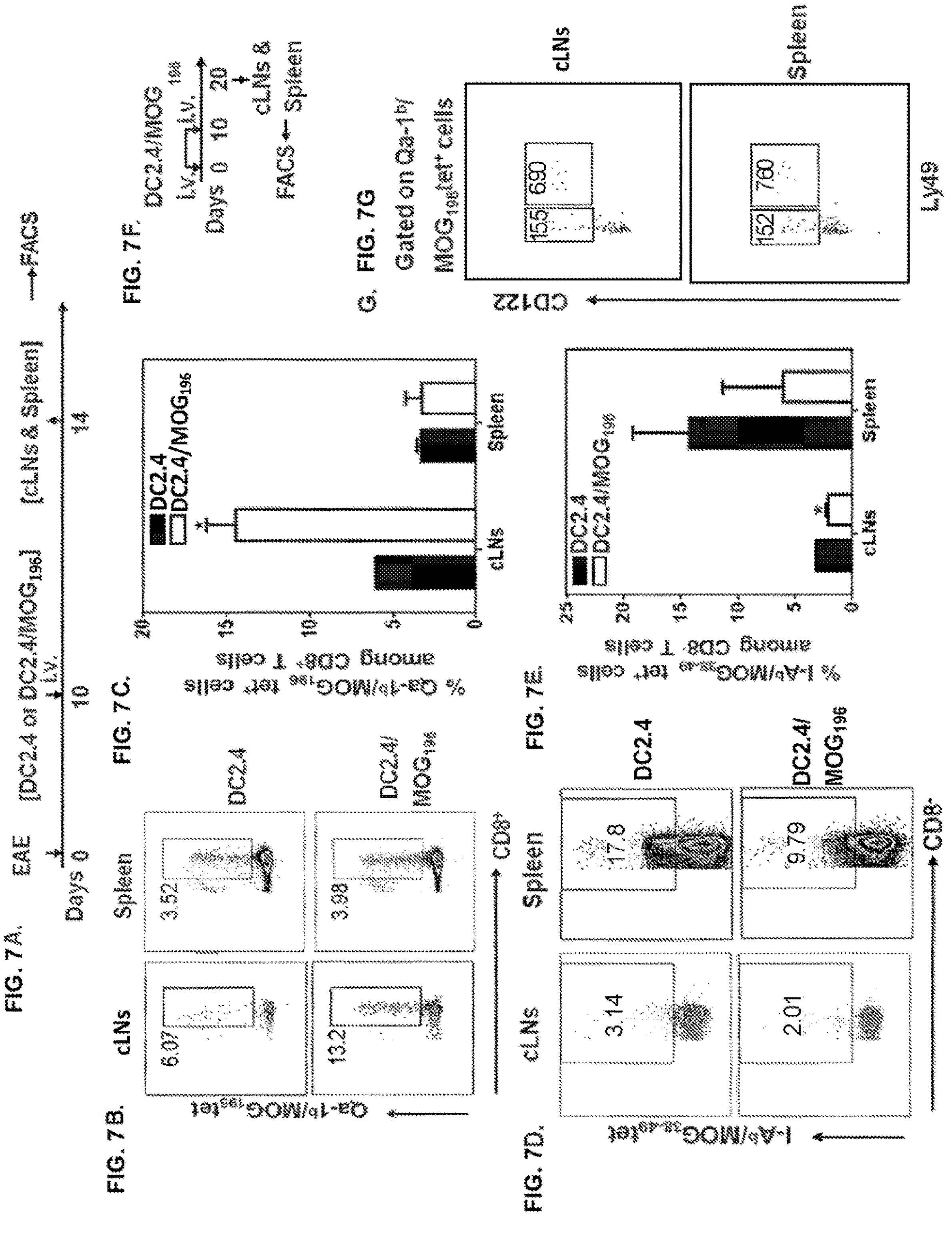
FIG. 7A-7G. Immunization with DCs pulsed with $MOG_{196}$ activates Qa-$1^b$/$MOG_{196}$ tetramer$^+$ cells that specifically accumulate in cervical lymph nodes. (A) C57BL/6 mice (5 mice/group) were immunized with $MOG_{35-55}$ for EAE. Ten days later, when paralytic symptoms began, animals received one intravenous immunization with mitomycin C-treated DC2.4 or $MOG_{196}$-pulsed DC2.4 (DC2.4/$MOG_{196}$). Four days later, mononuclear cells prepared from spleens and cervical lymph nodes were examined for the presence of Qa-$1^b$/$MOG_{196}$ and 1-Ab/$MOG_{38-49}$ tetramer$^+$ cells by flow cytometry. (B) Representative plots of Qa-$1^b$/$MOG_{196}$tetramer$^+$ cells among CD8$^+$ T cells in cervical lymph nodes and spleens. (C) Cumulative data of Qa-$1^b$/$MOG_{196}$tetramer$^+$ cells from five mice. *P<0.05. Two-way ANOVA test. (D) Representative plots of I-$A^b$/$MOG_{38-49}$ tetramer$^+$ cells among CD8$^-$ T cells in cervical lymph nodes and spleens. (E) Cumulative data of I-$A^b$/$MOG_{38-49}$ tetramer$^+$ cells from five mice. *P<0.05. Two-way ANOVA test. (F) Experimental design for "G": C57BL/6 mice were intravenously immunized with $MOG_{196}$-pulsed DC2.4 cells at days 0 and 10. Ten days after the last immunization, mononuclear cells from cervical lymph nodes and spleens were examined for the expressions of CD122 and Ly49 on Qa-$1^b$/$MOG_{196}$ tetramer$^+$CD8$^+$ T cells by flow cytometry. (G) Representative FACS plots from two independent experiments were shown.

Immunization with $MOG_{196}$-pulsed DCs activated Qa-$1^b$/$MOG_{196}$tetramer+ cells that accumulated in the cervical lymph nodes in EAE-bearing animals. Next, it was investigated whether immunization with $MOG_{196}$-pulsed DCs indeed activated Qa-$1^b$/$MOG_{196}$tetramer+ cells in vivo in EAE-bearing animals. Hence, C57BL/6 mice were induced for EAE. Ten days later, when the paralytic disease began, animals received mature DC2.4 cells (a bone-marrow-derived DC line) or $MOG_{196}$-pulsed DC2.4 cells (DC2.4/$MOG_{196}$). Four days after the treatments, spleens and cervical lymph nodes were analyzed for the presence of Qa-1b/$MOG_{196}$tetramer+ cells. The data showed that percent of Qa-$1^b$/$MOG_{196}$tetramer+ cells in spleens between the two treatments was similar, while percent of tetramer+ cells in cervical lymph nodes following the DC2.4/$MOG_{196}$ treatment, as compared to DC2.4 treatment, was significantly elevated (FIGS. 7A, 7B and 7C). The data suggested that the Qa-$1^b$/$MOG_{196}$ tetramer+ cells specifically accumulated in the CNS in EAE-bearing animals. In contrast, I-Ab/$MOG_{38-49}$ tetramer+ cells, which detected $MOG_{35-55}$-reactive pathogenic autoimmune cells, were significantly reduced in cervical lymph nodes (FIGS. 7A, 7D, and 7E). The data were consistent with suppression of ongoing paralytic disease following DC2.4/$MOG_{196}$ treatment (FIG. 6).

CD122 and Ly49 were expressed in a portion of the Qa-$1^b$/$MOG_{196}$ tetramer+ cells. Recent data suggest that Qa-1-restricted $CD8^+$ Treg cells are among $CD122^+Ly49^+$ $CD8^+$ T cells (Tang et al., *J. Immunol.,* 2006, 177:7645-7655; Kim et al., *Proc Natl. Acad Sci USA,* 2011, 108:2010-2015; Leavenworth et al., *J Clin Invest,* 2013, 123:1382-1389). Expression of these two markers on the Qa-$I^b$/$MOG_{196}$ tetramer+ cells was analyzed. The data showed that about 22.6% of the tetramer+ cells expressed CD122 and about 7.2% of the tetramer+ cells expressed both CD122 and Ly49 (FIG. 7F-7G). Therefore, the data suggest that CD122 and Ly49 are two markers for Qa-1-restricted $CD8^+$ Treg cells.

Figure 9:
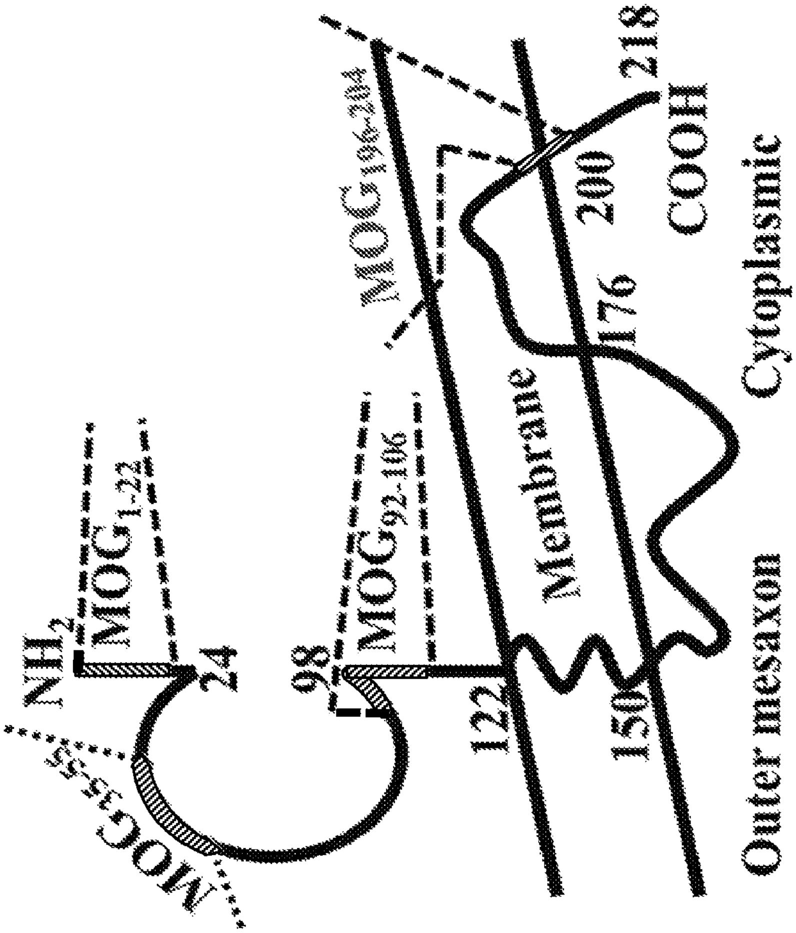
FIG. 9. $MOG_{196}$ sequence is located in the intracellular domain of myelin oligodendrocyte glycoprotein (MOG). The three highlighted extracellular epitopes, $MOG_{35-55}$, $MOG_{1-22}$, and $MOG_{92-106}$, are encephalogenic (or pathogenic) epitopes. The intracellular $MOG_{196}$ epitope is a regulatory (or protective) Qa-$1^b$ epitope.

$MOG_{196}$ is evolutionarily conversed and unique to MOG. Some known Qa-1-binding peptides, e.g., Qdm and HSP60p216, bind to both Qa-1 and HLA-E (Miller et al., *J. Immunol.,* 2003, 171:1369-1375). In addition, peptide binding motifs of Qa-1 and HLA-E are similar (Miller et al., supra; Kurepa et al., *J. Immunol.,* 1997, 158:3244-3251). It was investigated whether the $MOG_{196}$ peptide sequence was evolutionarily conserved. A Blast search of GenBank protein sequence data showed that $MOG_{196}$ sequence was evolutionarily conserved (FIG. 8). Furthermore, sequence of $MOG_{196}$ is specific to MOG and located in the intracellular domain (FIG. 9). Therefore, HLA-E can be utilized to suppress MS in a similar manner as Qa-1 is used to suppress EAE.

Figure 10:
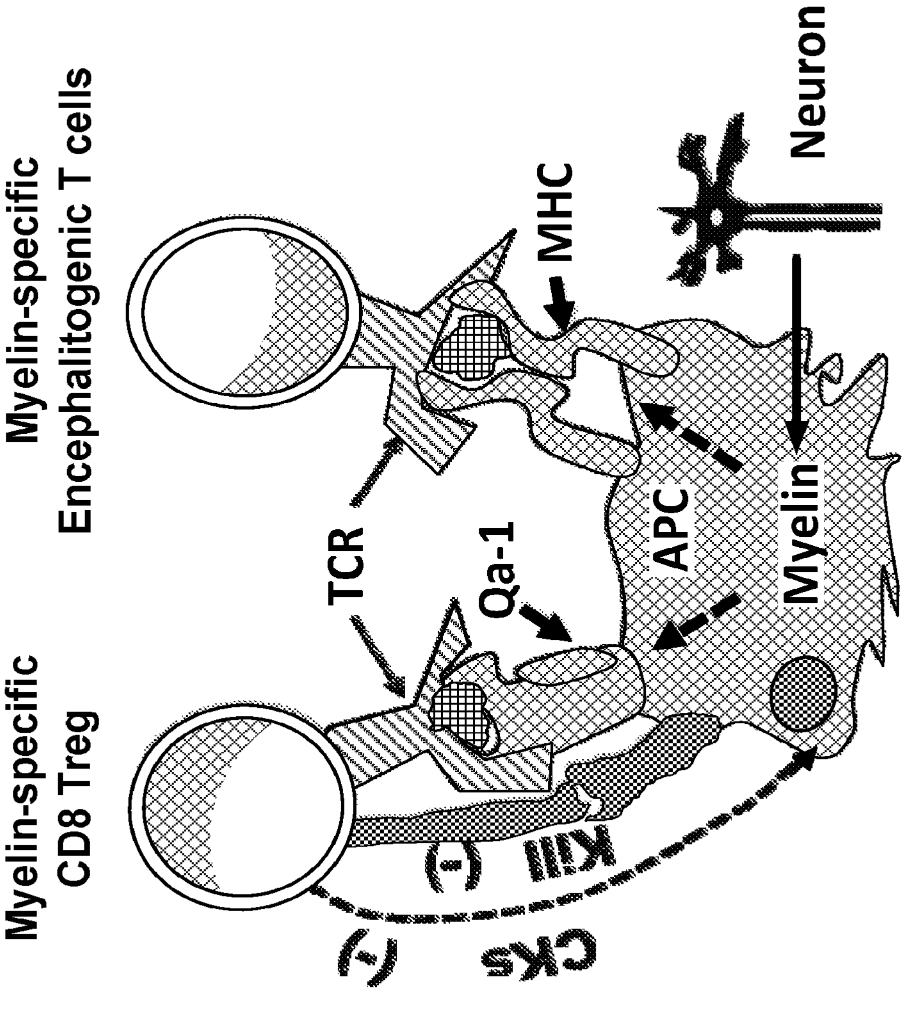
FIG. 10. A model of immune regulation mediated by myelin-specific, Qa-1-restricted CD8$^+$ Treg. Myelin-specific, Qa-1-restricted CD8$^+$ Treg cells can recognize and tolerize/eliminate antigen-presenting cells (APCs) that otherwise activate myelin-specific encephalitogenic T cells in the CNS and/or peripheral lymphoid tissues. Tolerization/elimination of APCs, which present myelin epitopes, is mediated by regulatory cytokines (CKs), inhibitory molecules, or direct cytotoxicity. Consequently, activation of myelin-specific encephalitogenic T cells and autoimmune attacks of myelin sheath are thwarted.

Proposed mechanism underlying the disease suppression mediated by the myelin-specific, Qa-1 (HLA-E)-restricted $CD8^+$ Treg cells. Previous data suggest that disease suppression involves IFN-γ, perform, and IL-15. These data support a direct killing of target cells by the Qa-1-restricted $CD8^+$ Treg cells. Since oligodendrocytes normally do not express MHC molecules (Goverman, *Nat Rev Immunol,* 2009, 9:393-407), it may explain that the $MOG_{196}$-specific Qa-1-restricted $CD8^+$ Treg cells do not damage myelin. Thus, the same antigen presenting cell, which phagocytoses myelin, can present both pathogenic and regulatory myelin epitopes to pathogenic $CD4^+$ and regulatory $CD8^+$ T cells respectively because both epitopes are located in the myelin (FIG. 10). In this regard, recognition of the regulatory Qa-1/HLA-E myelin epitopes by the $CD8^+$ Treg cells leads to 1) elimination of and/or induction of tolerance in the antigen-presenting cells; 2) elimination and/or induction of tolerance in encephalitogenic T cells that have obtained the epitope complexes from antigen-presenting cells via a process called trogocytosis. Consequently, activation and proliferation of encephalitogenic T cells are thwarted and autoimmune attacks of myelin sheath are stopped.

Since it has been demonstrated that $MOG_{196}$ (i.e., the regulatory Qa-1 epitope) and $MOG_{35-55}$ (i.e., the pathogenic epitope) are both located in MOG that is the autoantigen (FIG. 10), the two types of epitopes should be presented by the same APCs. Consequently, $MOG_{196}$-specific Qa-1-restricted $CD8^+$ Treg, functionally enhanced by $MOG_{196}$ immunization, can specifically recognize and suppress APCs that have phagocytosed MOG and otherwise initiated or perpetuated EAE.

DISCUSSION

The present disclosure provides evidence of an evolutionarily conserved regulatory Qa-1 epitope, $MOG_{196}$, in mouse myelin oligodendrocyte glycoprotein (MOG). The discovery of the regulatory Qa-1 epitope in MOG is significant for several reasons. First, it reveals another potential regulatory pathway wherein Qa-1-restricted $CD8^+$ Treg cells, besides targeting autoreactive T cells, may also target an autoantigen to suppress an autoimmune disease. Second, because of their specificity for an autoantigen, Qa-1-restricted $CD8^+$ Treg cells activated by a regulatory Qa-1 epitope derived from an autoantigen, as compared to autoreactive T cells, may potentially accumulate in the diseased tissues and thereby more efficiently suppress autoimmune attacks. Third, because more autoantigens have been discovered in various autoimmune diseases and because generation of autoreactive T cells is lengthy and tedious, autoantigens are more accessible than autoreactive T cells.

Immunization with $MOG_{196}$-pulsed immunogenic dendritic cells robustly suppressed EAE, which was abrogated by depletion of $CD8^+$ T cells. Therefore, immunization with DCs pulsed with myelin-derived HLA-E epitopes has been shown to enhance function of myelin-specific HLA-E-restricted $CD8^+$ Treg cells and thus represents a novel antigen-specific therapy for MS.

Studies of Qa-1 (HLA-E)-mediated antigen-specific therapies have been focused on targeting pathogenic autoimmune $CD4^+$ T cells. Because efficient entering of $CD8^+$ T cells into CNS depends on presentation of CNS-antigens at the blood-brain barrier (BBB) (Galea et al., *J. Exp. Med,* 2007, 204:2023-2030), Qa-1-restricted $CD8^+$ Treg cells which target epitopes in pathogenic autoimmune $CD4^+$ T cells may not efficiently accumulate in the CNS due to a lack of specificity for CNS and therefore may predominantly suppress the pathogenic $CD4^+$ T cells in the peripheral lymphoid organs. In contrast, myelin-specific Qa-1-restricted $CD8^+$ Treg cells described here will have the advantage to cross the BBB and provide in situ suppression of demyelinating inflammation in the CNS. To support this notion, the data herein shows that, in the course of EAE, $MOG_{196}$-specific, Qa-1-restricted $CD8^+$ Treg cells specifically accumulated in the cervical lymph nodes (i.e., the draining lymph nodes for CNS).

With respect to potential mechanisms underlying the disease suppression mediated by the myelin-specific, Qa-1 (HLA-E)-restricted $CD8^+$ Treg cells, the disease suppression involves IFN-γ, perform, and IL-15 (Beeston et al., *J. Neuroimmunol.,* 2010, 229:91-97; Kim et al., *Nature,* 2010, 467:516-523). These data support a direct killing of target cells by the Qa-1-restricted $CD8^+$ Treg cells. Since oligodendrocytes normally do not express MHC molecules (Goverman, *Nat Rev Immunol,* 2009, 9:393-407), it may explain that the $MOG_{196}$-specific Qa-1-restricted $CD8^+$ Treg cells do not damage myelin. It is proposed that the same antigen presenting cell, which phagocytoses myelin, can present both pathogenic and regulatory myelin epitopes to pathogenic $CD4^+$ and regulatory $CD8^+$ T cells respectively because both epitopes are located in the myelin (FIG. 10). In this regard, recognition of the regulatory Qa-1/HLA-E myelin epitopes by the $CD8^+$ Treg cells leads to 1) elimination of and/or induction of tolerance in the antigen-presenting cells; 2) elimination and/or induction of tolerance in encephalitogenic T cells that have obtained the epitope complexes from antigen-presenting cells via a process called trogocytosis. Consequently, activation and proliferation of encephalitogenic T cells are thwarted and autoimmune attacks on myelin sheath are stopped.

A recent finding showed that neuroantigen-specific $CD8^+$ T cells are regulatory. See, Ortega et al., *Neural Neuroimmnunol Neuroinflamm,* 2015, 2:e170. However, the neuroantigen-specific $CD8^+$ Treg cells differ from myelin-specific Qa-1-restricted $CD8^+$ Treg cells in requiring classical MHC I molecules for presentation. In addition, priming of the neuroantigen-specific $CD8^+$ Treg cells requires the presence of regulatory and pathogenic epitopes m the same myelin protein. This second characteristic suggests that active immunization with such a regulatory neuroantigenic epitope is not a suitable therapy for MS. In contrast, the myelin-specific $CD8^+$ Treg cells described here can be primed through active immunization with DCs pulsed with the regulatory epitope alone.

All publications and patents cited in this specification are herein incorporated by reference as if each individual publication or patent were specifically and individually indicated to be incorporated by reference and are incorporated herein by reference to disclose and describe the methods and materials in connection with which the publications are cited.

The inventions have been described broadly and generically herein. Each of the narrower species and subgeneric groupings falling within the generic disclosure also form part of the invention. In addition, where features or aspects of the invention are described in terms of Markush groups, those skilled in the art will recognize that the invention is also thereby described in terms of any individual member or subgroup of members of the Markush group.

It should be understood that although the present invention has been specifically disclosed by certain aspects, embodiments, and optional features, modification, improvement, and variation of such aspects, embodiments, and optional features can be resorted to by those skilled in the art, and that such modifications, improvements, and variations are considered to be within the scope of this disclosure.

What is claimed is:

1. A composition, comprising a dendritic cell and a myelin oligodendrocyte glycoprotein (MOG) peptide, wherein:

the MOG peptide comprises the sequence of amino acids set forth in any of SEQ ID NOs:1-19;

the MOG peptide is a MOG-specific non-classical major histocompatibility complex 1b (MHC1b) epitope;

the MOG-specific MHC1b epitope is presented by the dendritic cell to thereby activate regulatory CD8+ T cells in vitro and in vivo; and the dendritic cell was pulsed with the MOG-specific MHC1b epitope to produce the composition.

2. The composition of claim 1, wherein the peptide activates HLA-E-restricted regulatory CD8+ T cells in vitro or in vivo.

3. The composition of claim 1, wherein the peptide comprises a HLA-E epitope.

4. The composition of claim 1, wherein the peptide consists of the sequence of amino acids set forth in any of SEQ ID NOs:1-19.

5. The composition of claim 1, wherein the peptide comprises the sequence of amino acids set forth in SEQ ID NO:1 (IICYNWLHR).

6. The composition of claim 1, wherein the peptide consists of the sequence of amino acids set forth in SEQ ID NO:1 (IICYNWLHR).

7. The composition of claim 1, wherein the dendritic cells are derived from a multiple sclerosis subject.

8. The composition of claim 1, wherein the dendritic cells are derived from monocytes.

9. The composition of claim 1, wherein the dendritic cells are derived from bone marrow, cord blood, or peripheral blood.

10. The composition of claim 1, wherein the dendritic cells are derived from myelin-specific pathogenic autoimmune cells.

11. The composition of claim 5, wherein the dendritic cells are derived from a multiple sclerosis subject.

12. The composition of claim 5, wherein the dendritic cells are derived from monocytes.

13. The composition of claim 5, wherein the dendritic cells are derived from bone marrow, cord blood, or peripheral blood.

14. The composition of claim 5, wherein the dendritic cells are derived from myelin-specific pathogenic autoimmune cells.

15. The composition of claim 1, wherein the dendritic cell and the MOG-specific MHC1b epitope were pulsed for 3 to 4 hours to produce the composition.

16. The composition of claim 5, wherein the dendritic cell and the MOG-specific MHC1b epitope were pulsed for 3 to 4 hours to produce the composition.

* * * * *